(12) United States Patent
Vanhamel et al.

(10) Patent No.: US 8,366,311 B2
(45) Date of Patent: Feb. 5, 2013

(54) SYSTEMS AND DEVICES FOR MIXING SUBSTANCES AND METHODS OF MAKING SAME

(75) Inventors: Steven Vanhamel, Velm (BE); Jean-Pascal Zambaux, Allonzier la Caille (FR); Tom Claes, Bilzen (BE)

(73) Assignee: ATMI BVBA, Hoegaarden (BE)

( * ) Notice: Subject to any disclaimer, the term of this patent is extended or adjusted under 35 U.S.C. 154(b) by 894 days.

(21) Appl. No.: 12/297,821

(22) PCT Filed: Apr. 21, 2007

(86) PCT No.: PCT/US2007/067163
§ 371 (c)(1),
(2), (4) Date: Apr. 20, 2009

(87) PCT Pub. No.: WO2008/005611
PCT Pub. Date: Jan. 10, 2008

(65) Prior Publication Data
US 2009/0323466 A1    Dec. 31, 2009

Related U.S. Application Data

(60) Provisional application No. 60/794,206, filed on Apr. 21, 2006.

(51) Int. Cl.
*B01F 7/16* (2006.01)
(52) U.S. Cl. .......... 366/102; 366/279; 366/331
(58) Field of Classification Search .......... 366/243, 366/255, 276, 277, 101, 102, 279, 331
See application file for complete search history.

(56) References Cited

U.S. PATENT DOCUMENTS

| | | | |
|---|---|---|---|
| 2,615,692 A | 10/1952 | Muller | |
| 2,877,994 A | 3/1959 | Jones | |
| 3,010,303 A | 11/1961 | Bochan | |
| 3,384,354 A * | 5/1968 | Migule et al. | 366/118 |
| 3,572,651 A * | 3/1971 | Harker | 366/185 |
| 3,647,397 A * | 3/1972 | Coleman | 366/167.1 |
| 3,802,470 A | 4/1974 | Coleman | |
| 3,913,895 A * | 10/1975 | De Bruyne | 366/247 |
| 3,955,802 A * | 5/1976 | de Bruyne | 366/343 |
| 3,998,435 A * | 12/1976 | de Bruyne | 366/243 |
| 4,112,518 A * | 9/1978 | Garlinghouse | 366/219 |
| 4,204,774 A * | 5/1980 | de Bruyne | 366/102 |
| 4,649,118 A * | 3/1987 | Anderson | 435/297.3 |
| 5,002,890 A | 3/1991 | Morrison | |
| 5,193,977 A | 3/1993 | Dame | |
| 5,362,642 A * | 11/1994 | Kern | 435/404 |

(Continued)

FOREIGN PATENT DOCUMENTS

| | | |
|---|---|---|
| DE | 1557130 A1 | 4/1970 |
| DE | 19705118 A1 | 8/1998 |

(Continued)

*Primary Examiner* — Tony G Soohoo
(74) *Attorney, Agent, or Firm* — Vincent K. Gustafson; Jenkins, Wilson, Taylor & Hunt, P.A.

(57) ABSTRACT

A mixing apparatus including a kinetic energy source, a mixing tank, a pivot guide, and transfer shaft is used to drive a mixing paddle through a circular path within a tank without substantial shaft rotation. Sleeved and sleeveless mixing paddles are provided in combination with sealable mixing tanks. A volumetric compensation system responsive to tank wall deflection is used to maintain the internal volume of a mixing tank within predetermined limits. One mixing apparatus includes multiple mixing shafts and paddles coupled to at least one kinetic energy source. Methods for fabricating sleeved paddle-containing mixing apparatuses are further provided.

28 Claims, 24 Drawing Sheets

U.S. PATENT DOCUMENTS

| | | | |
|---|---|---|---|
| 5,456,586 A | 10/1995 | Carson | |
| 5,633,165 A | 5/1997 | Swartz | |
| 5,941,635 A | 8/1999 | Stewart | |
| 5,988,422 A | 11/1999 | Vallot | |
| 6,071,005 A | 6/2000 | Ekambaram et al. | |
| 6,077,356 A | 6/2000 | Bouchard | |
| 6,178,925 B1 | 1/2001 | Sturm et al. | |
| 6,186,932 B1 | 2/2001 | Vallot | |
| 6,494,613 B2 | 12/2002 | Terentiev | |
| 6,634,783 B2 | 10/2003 | Baron | |
| 6,670,171 B2 * | 12/2003 | Carll | 435/289.1 |
| 6,837,610 B2 * | 1/2005 | Cadogan et al. | 366/144 |
| 6,844,186 B2 * | 1/2005 | Carll | 435/289.1 |
| 6,883,960 B2 * | 4/2005 | Reeder et al. | 366/243 |
| 7,025,234 B2 | 4/2006 | Priebe et al. | |
| 7,153,021 B2 * | 12/2006 | Goodwin et al. | 366/273 |
| 7,249,880 B2 * | 7/2007 | Zambaux | 366/277 |
| 7,431,494 B2 * | 10/2008 | Zambaux | 366/144 |
| 7,459,071 B2 * | 12/2008 | Omasa | 205/628 |
| 7,878,079 B2 * | 2/2011 | Goodwin | 73/863.81 |
| 2001/0039369 A1 | 11/2001 | Terentiev | |
| 2002/0105856 A1 | 8/2002 | Terentiev | |
| 2003/0226857 A1 | 12/2003 | Bibbo et al. | |
| 2003/0231546 A1 | 12/2003 | Bibbo et al. | |
| 2004/0027912 A1 | 2/2004 | Bibbo et al. | |
| 2004/0062140 A1 * | 4/2004 | Cadogan et al. | 366/144 |
| 2005/0002274 A1 | 1/2005 | Terentiev | |
| 2005/0078552 A1 | 4/2005 | Zambaux | |
| 2005/0239199 A1 | 10/2005 | Kunas et al. | |
| 2006/0131765 A1 | 6/2006 | Terentiev et al. | |
| 2008/0031082 A1 | 2/2008 | Zambaux | |

FOREIGN PATENT DOCUMENTS

| | | |
|---|---|---|
| DE | 102004013078 A1 | 10/2005 |
| GB | 1464733 A | 2/1977 |
| JP | 51-057064 A | 5/1976 |
| JP | 59-094696 A | 5/1984 |
| JP | 63-046759 U | 3/1988 |
| JP | 07-108154 A | 4/1995 |
| JP | 08-155950 A | 6/1996 |
| JP | 08-318148 A | 12/1996 |
| JP | 10-337461 A | 12/1998 |
| JP | 11-267488 A | 10/1999 |
| JP | 2003-002393 A | 1/2003 |
| NL | 8203579 | 4/1984 |
| WO | 2007050971 A1 | 5/2007 |

* cited by examiner

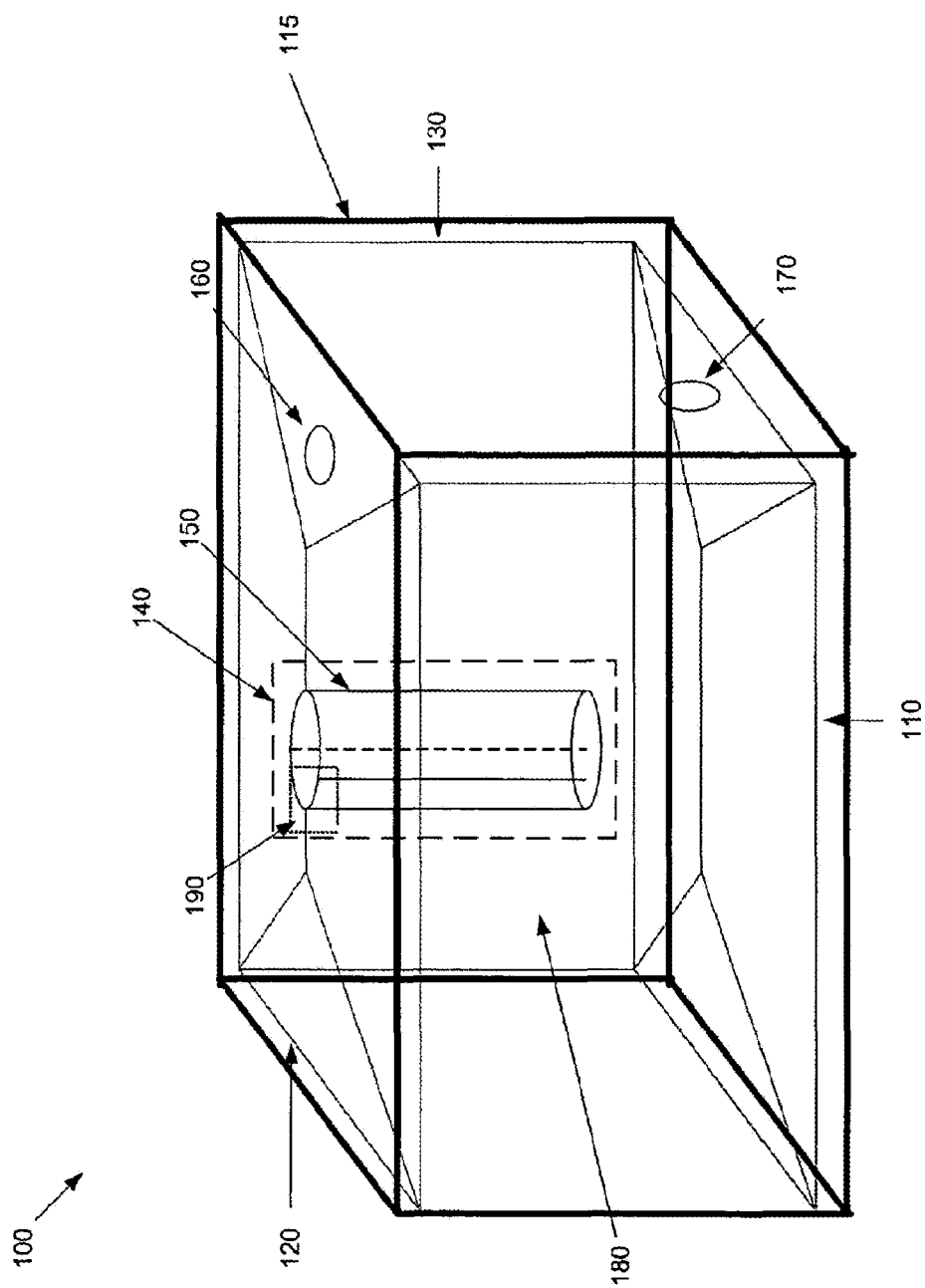
FIG_1

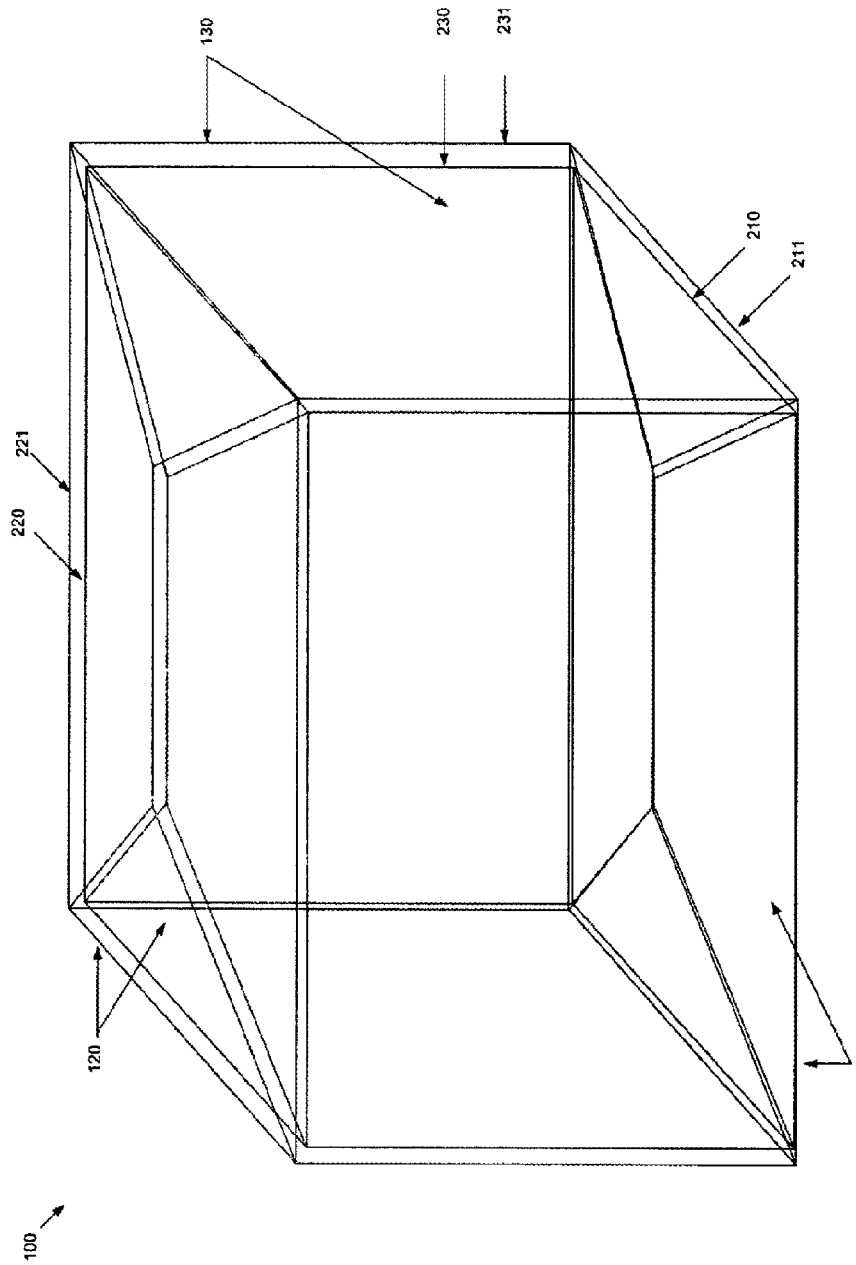
FIG._2

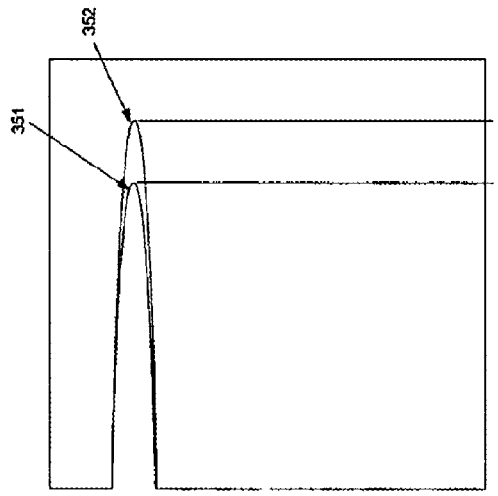
FIG._3B
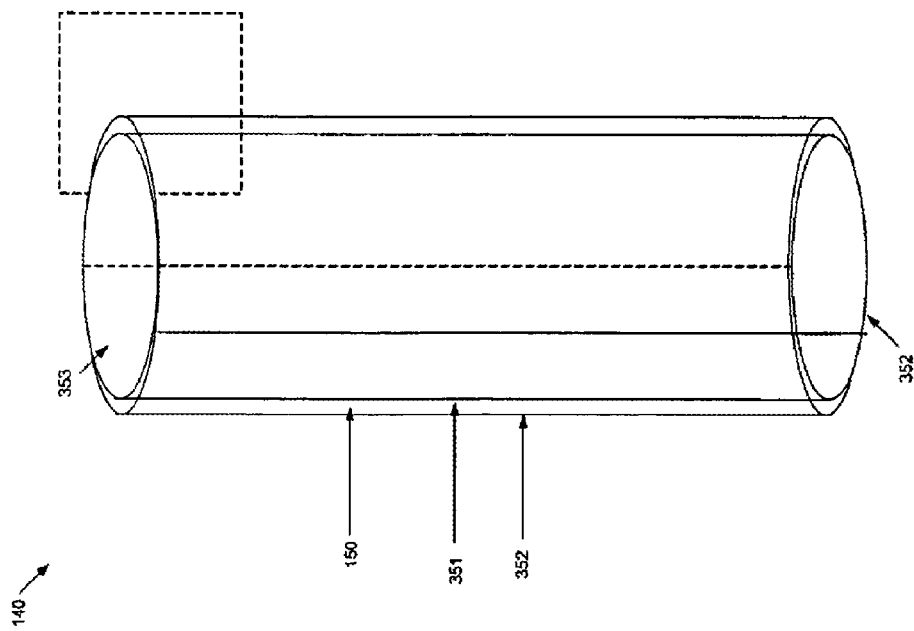
FIG._3A

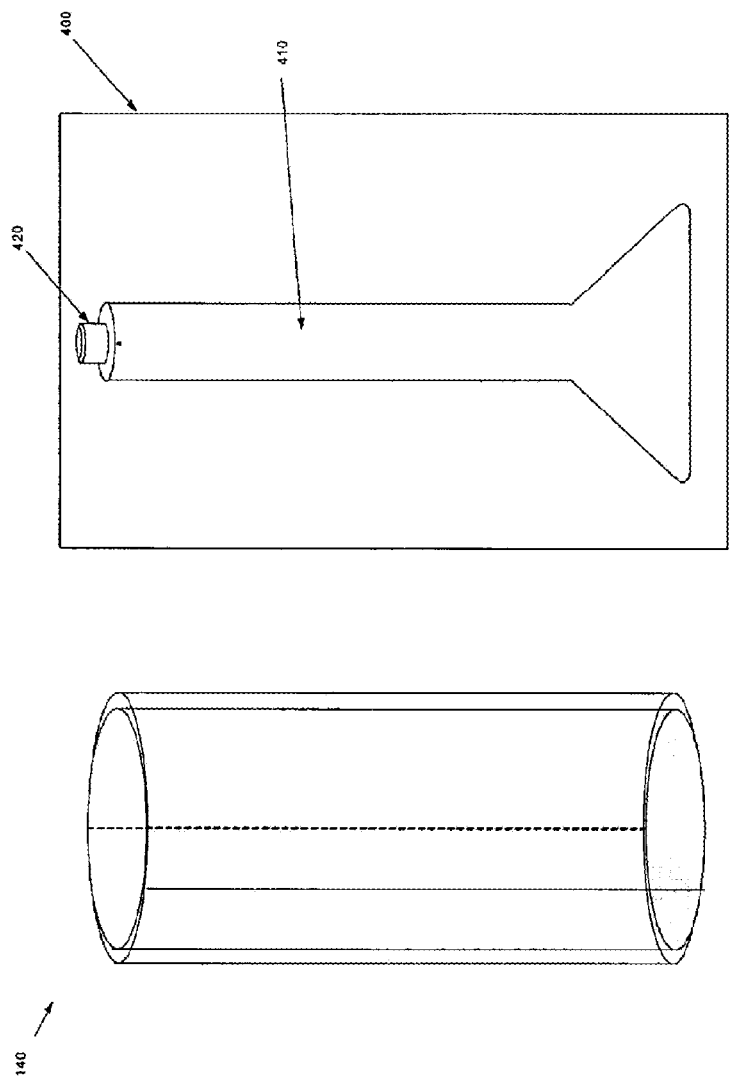
FIG._4A

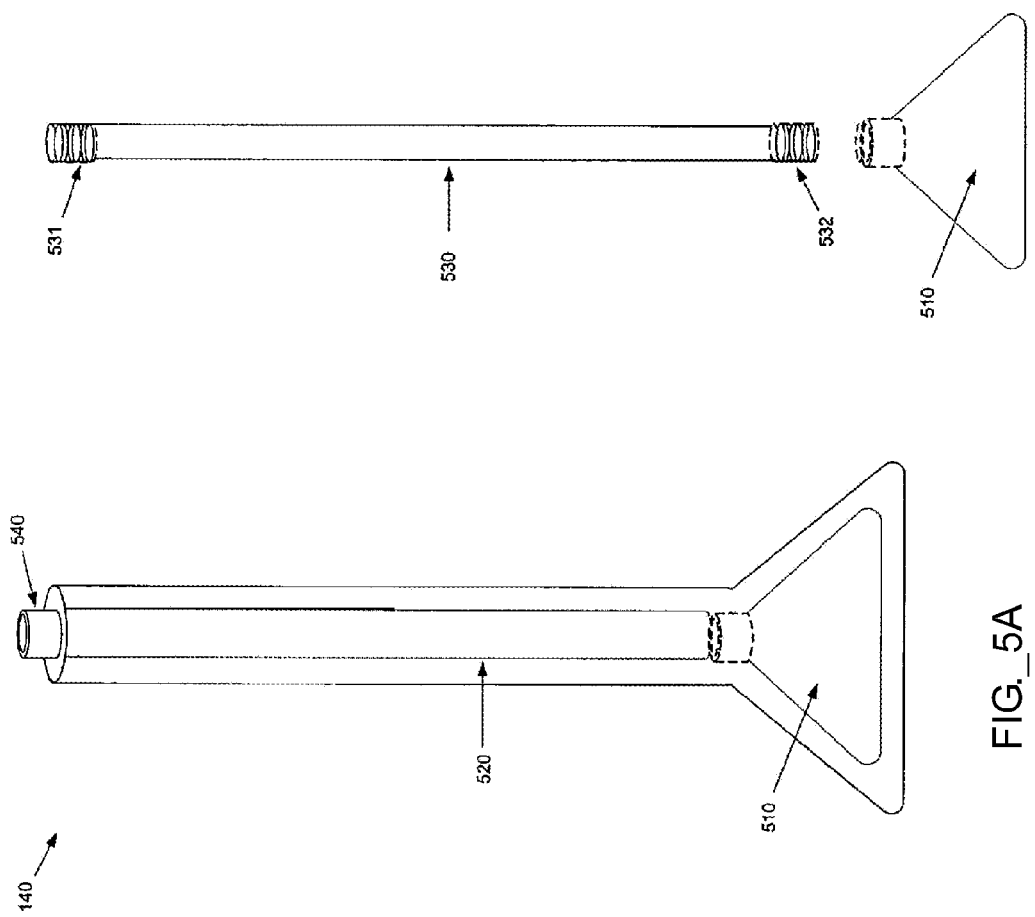
FIG._5A

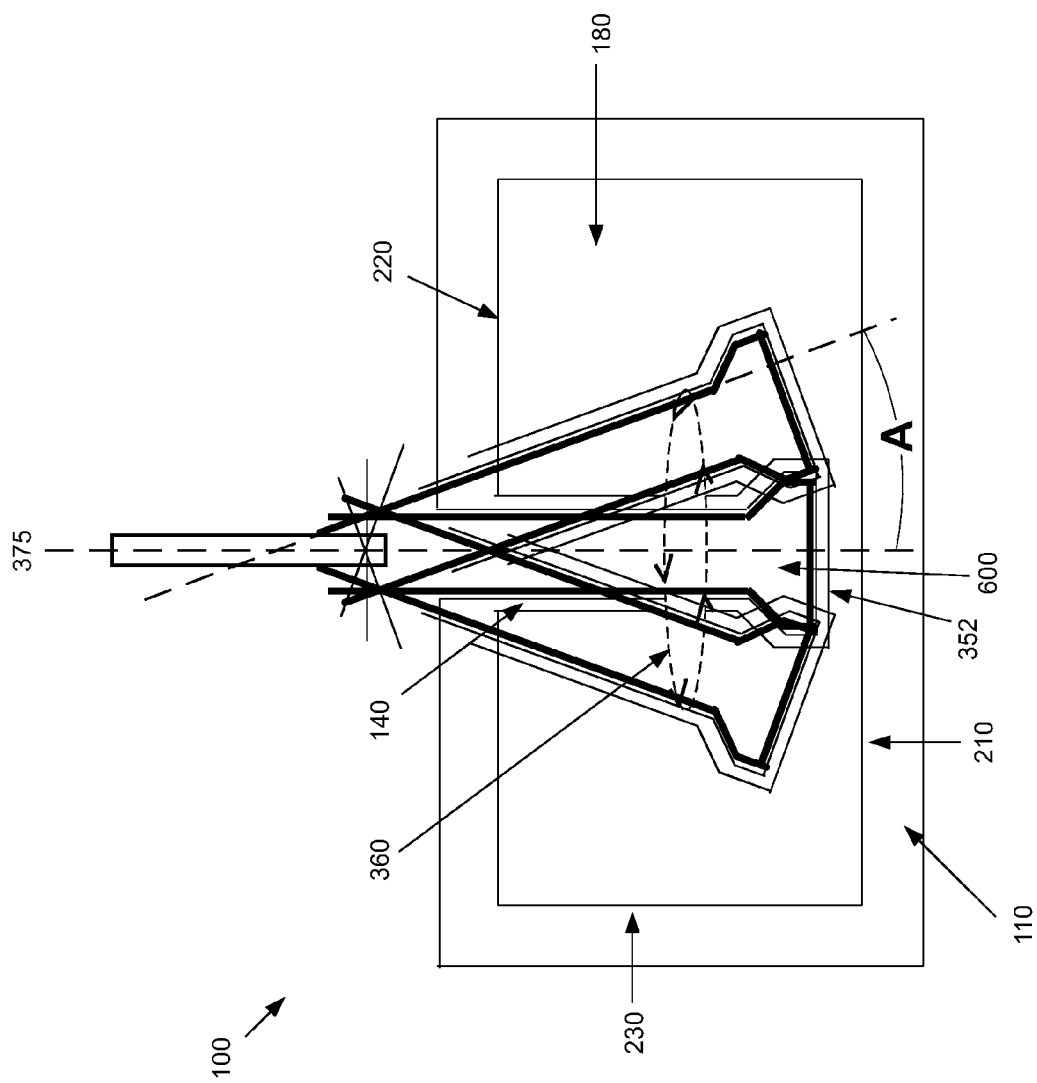

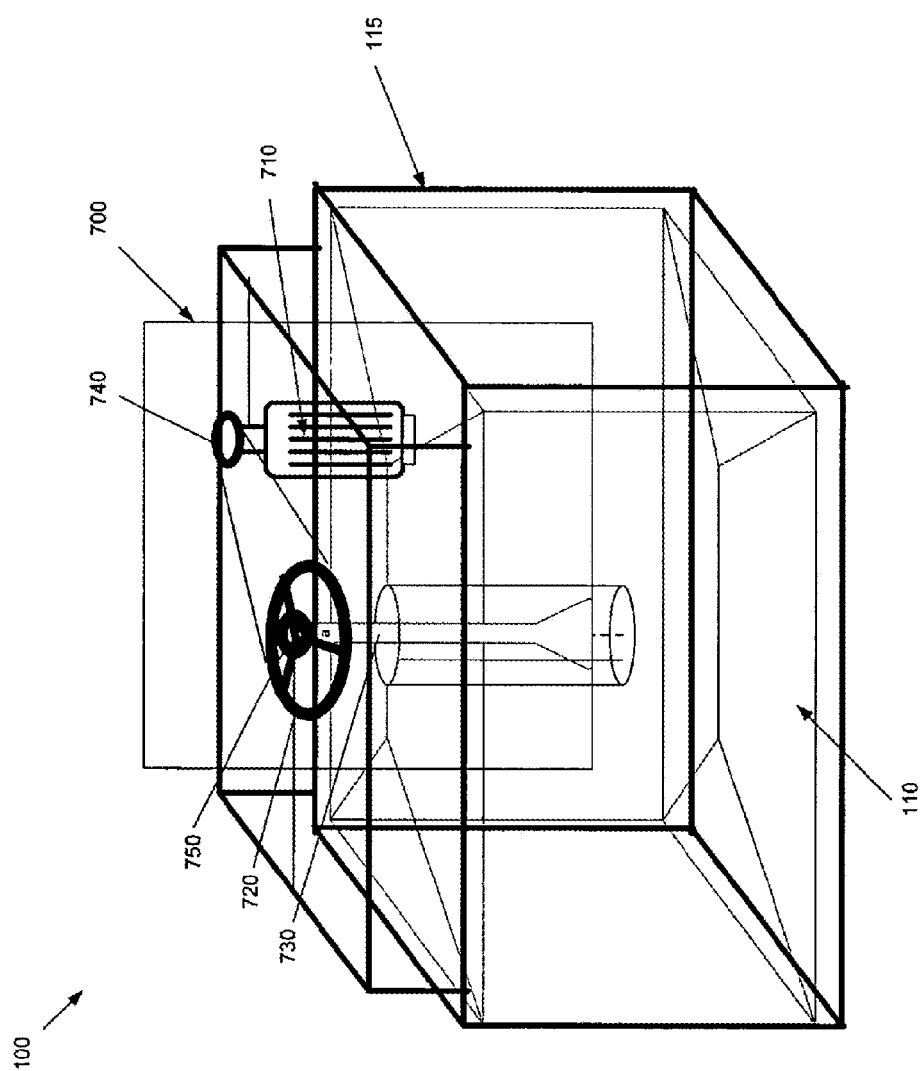
FIG._7

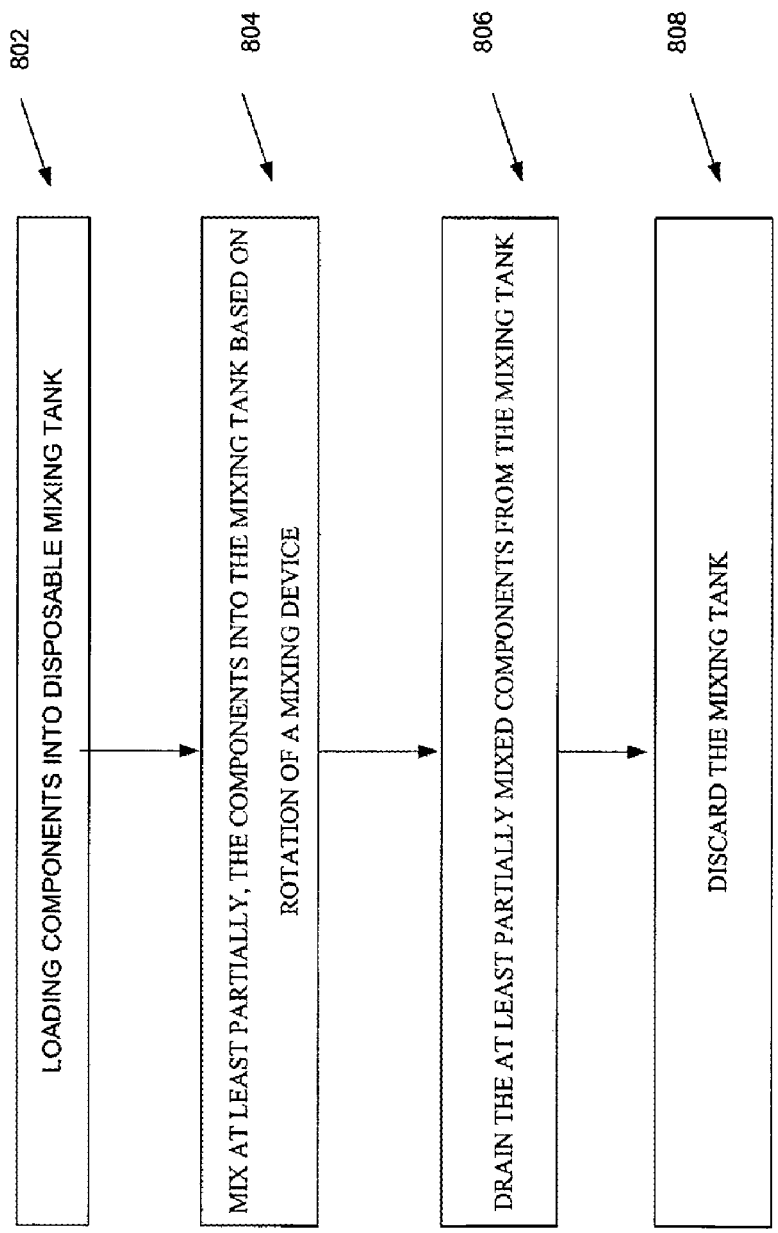
FIG._8

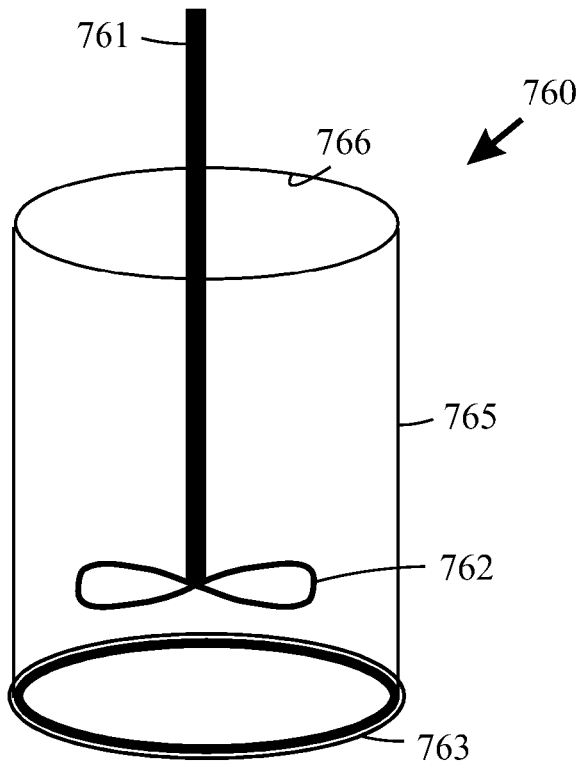
FIG._9
(PRIOR ART)
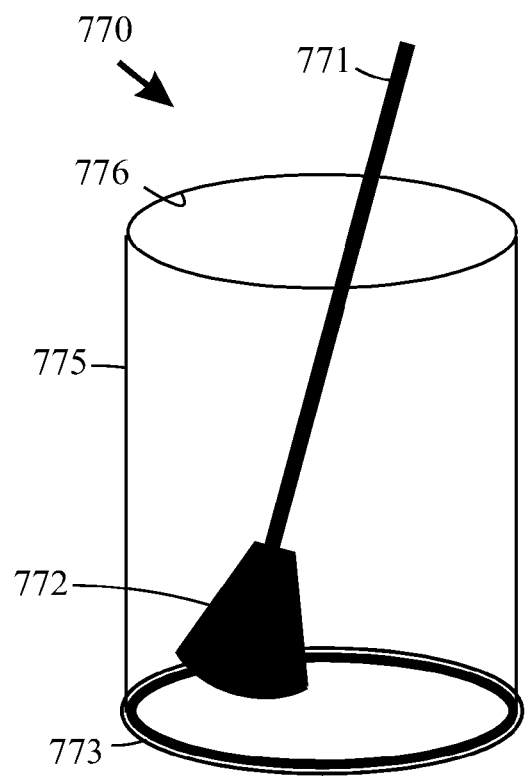
FIG._10

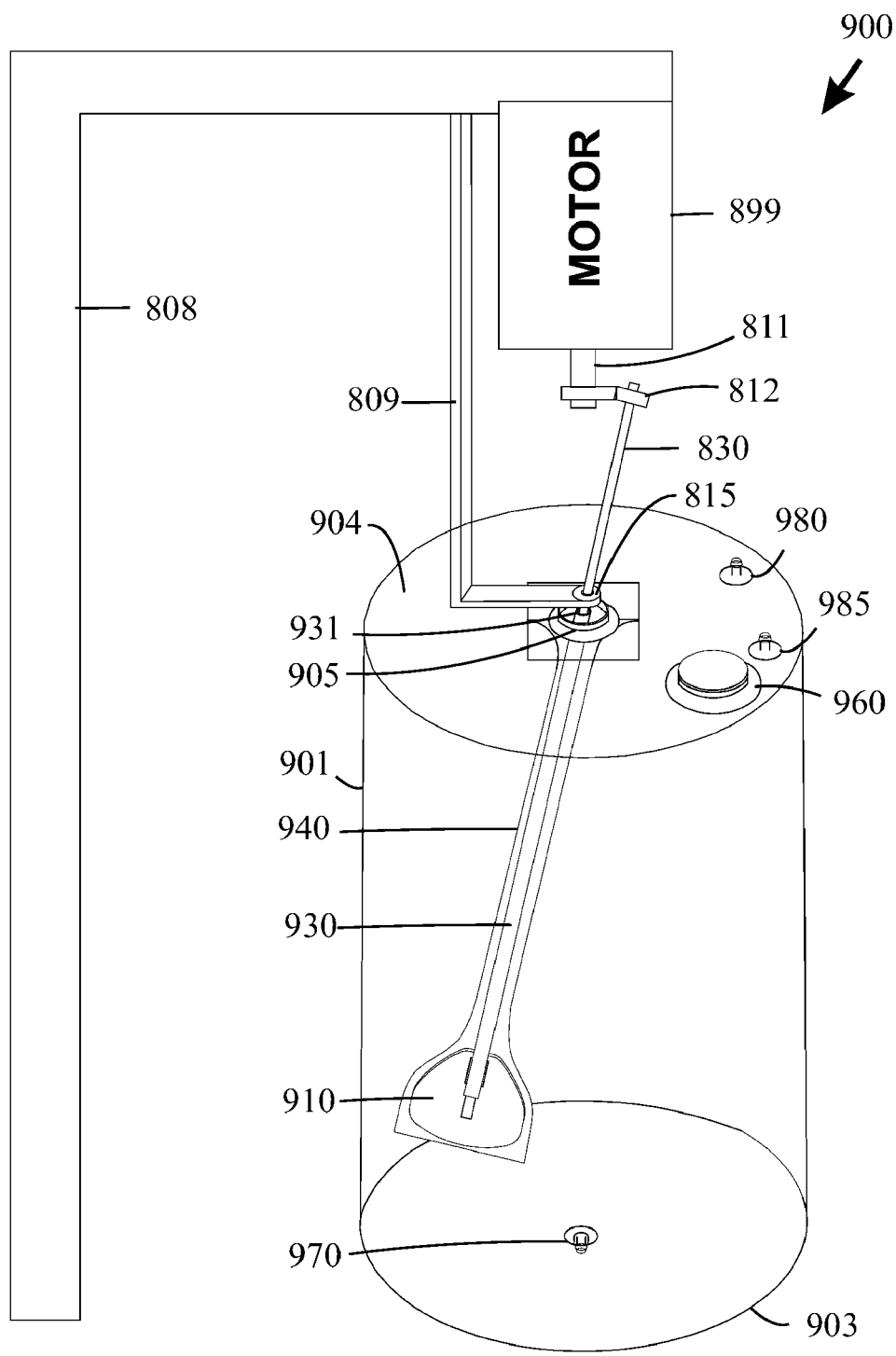
FIG._11A

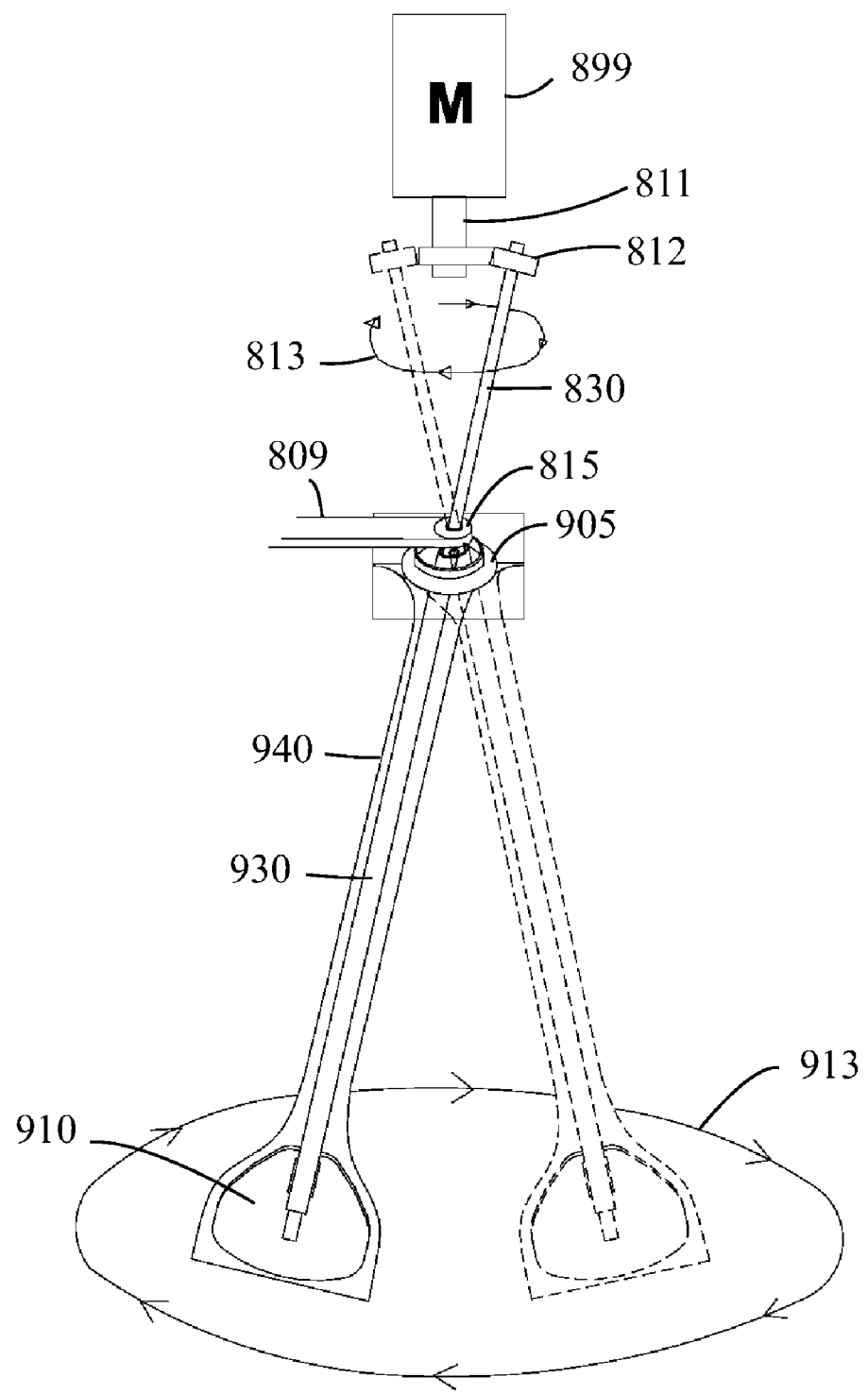
FIG._11B

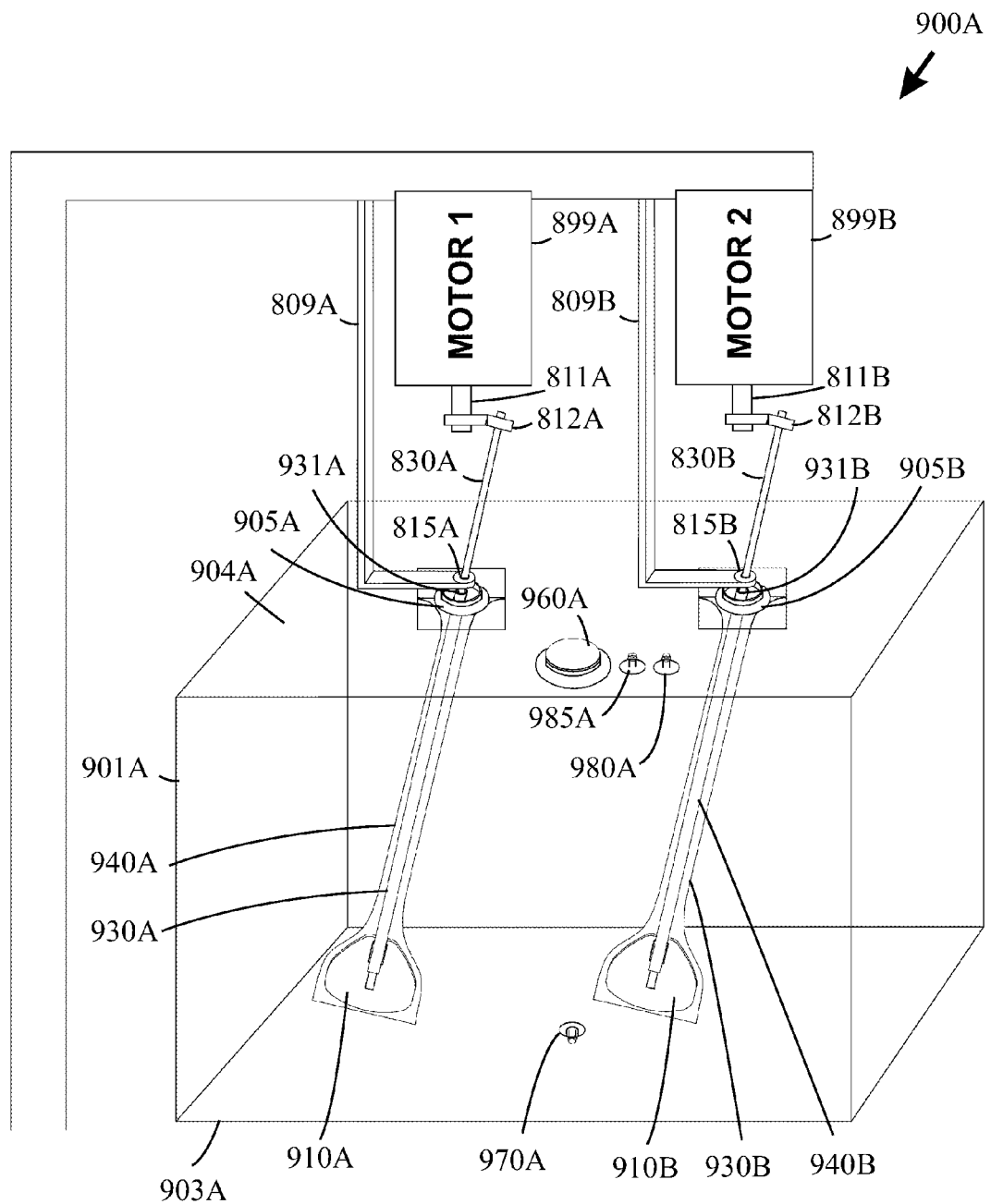
FIG._12A

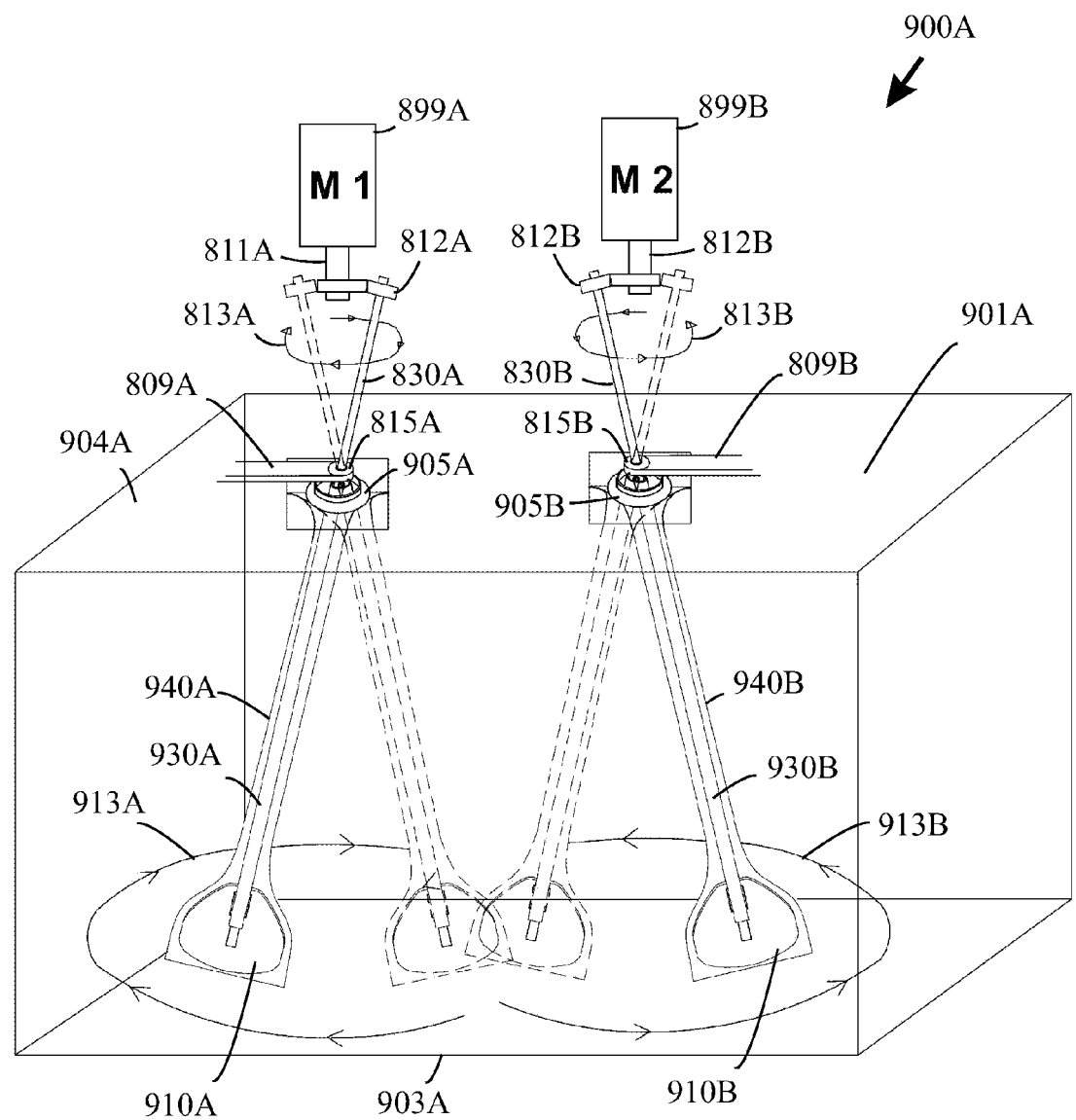
FIG._12B

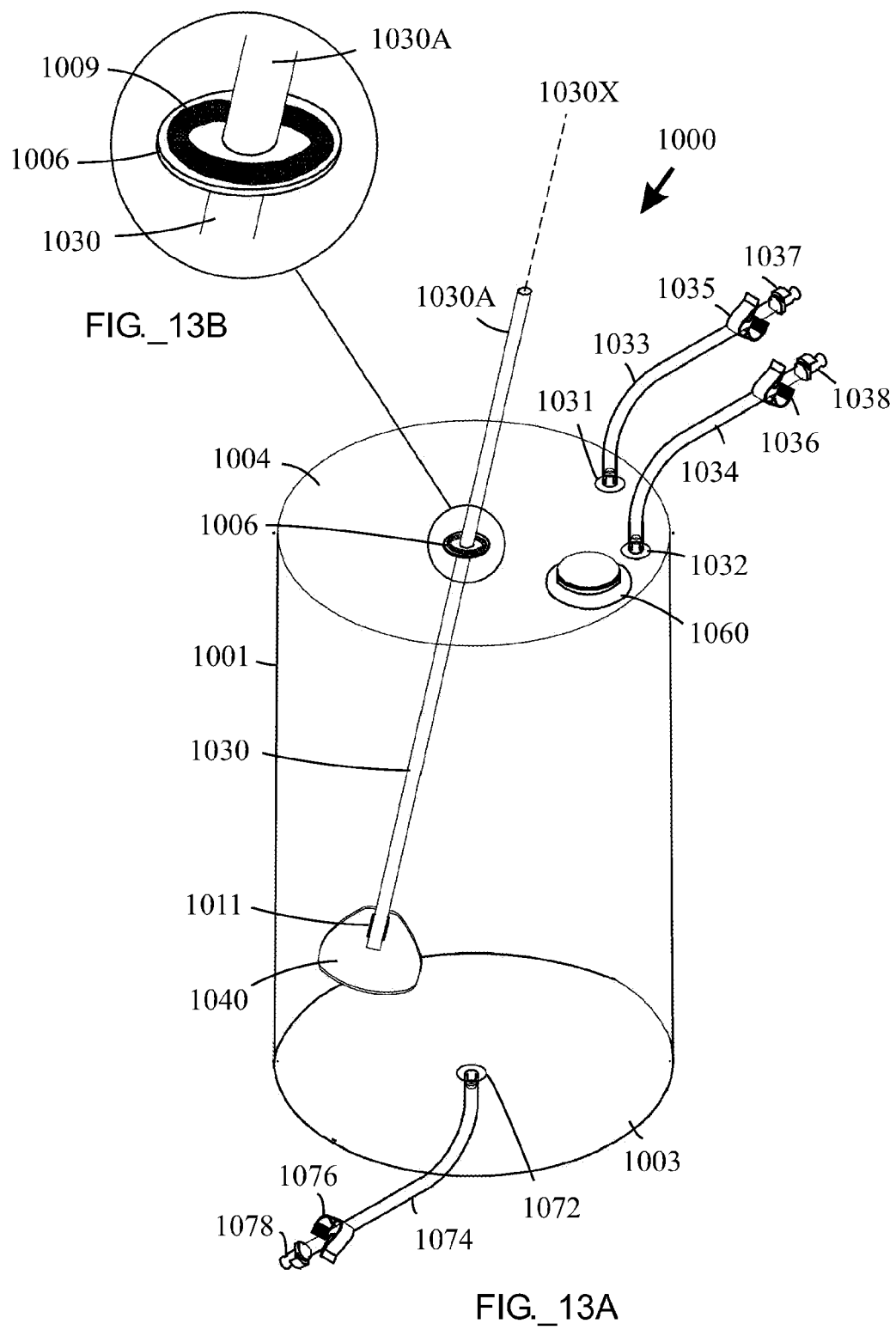
FIG._13B
FIG._13A

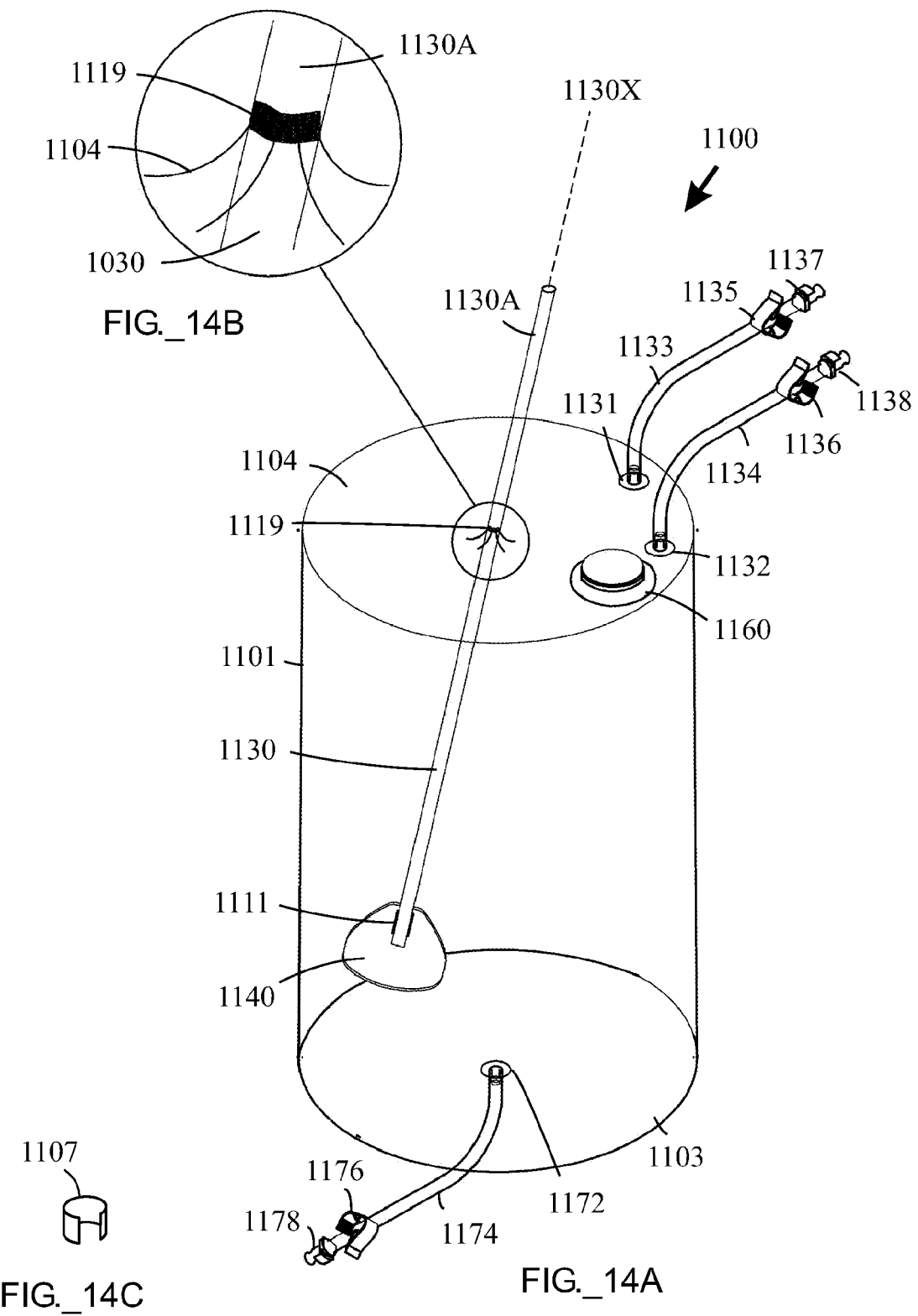
FIG._14B
FIG._14C
FIG._14A

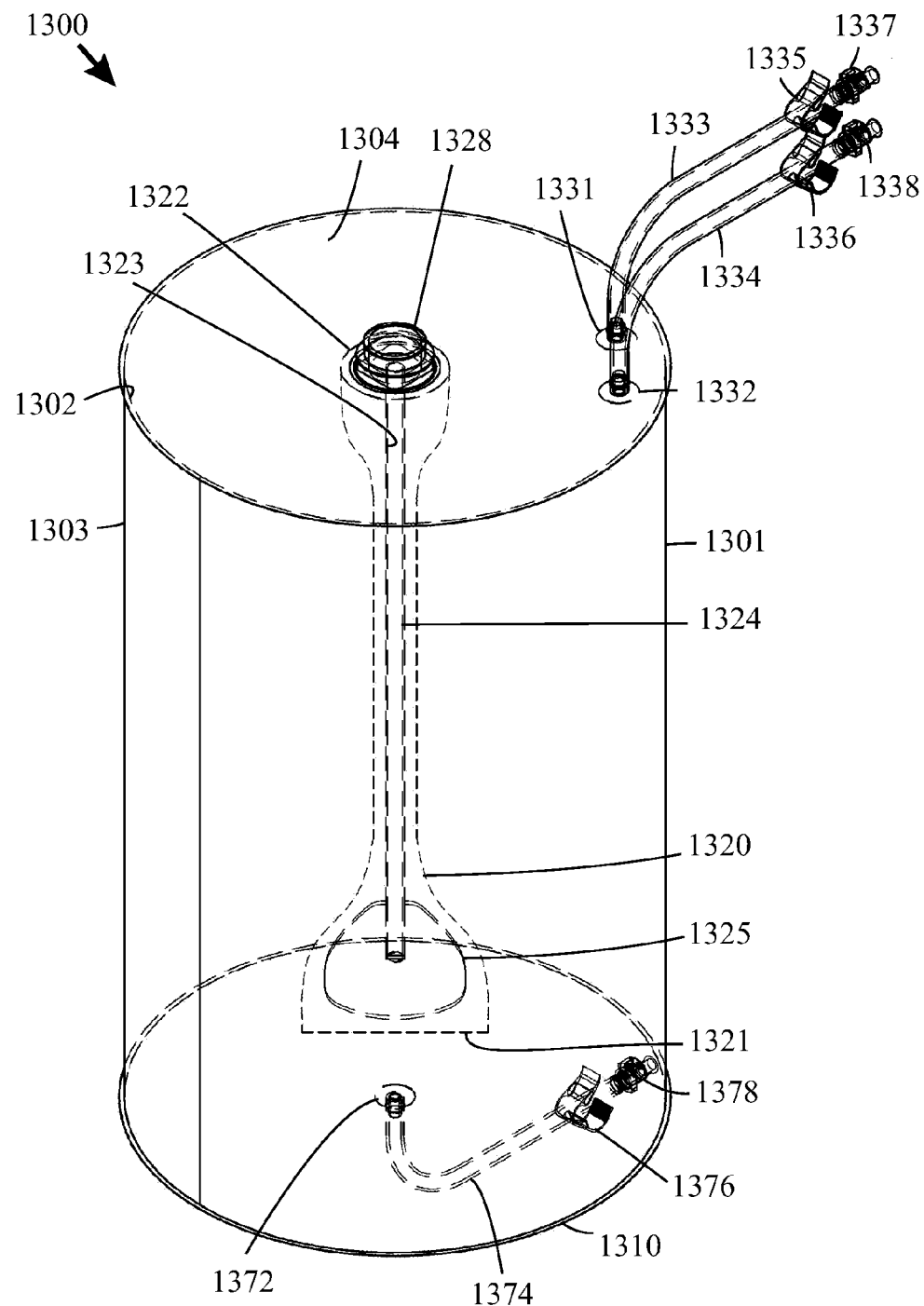
FIG._15

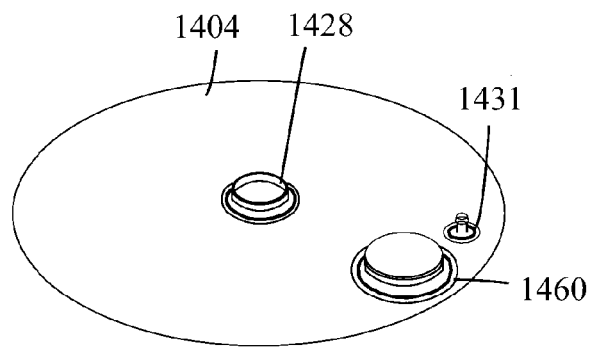
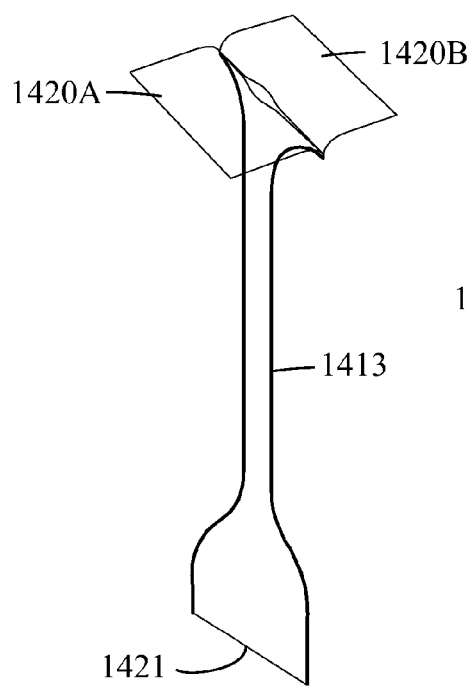
FIG._16A
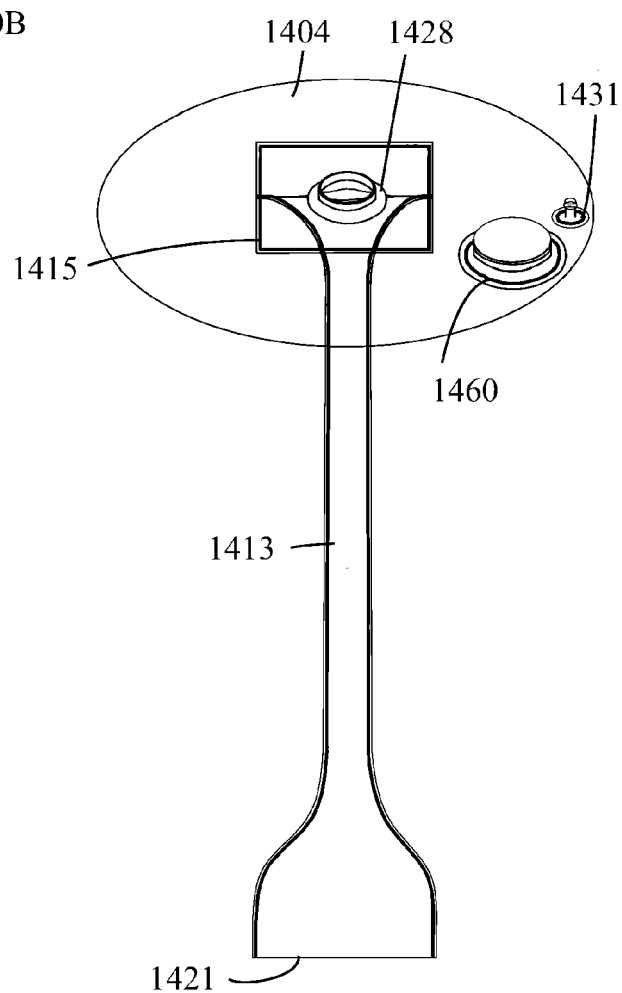
FIG._16B

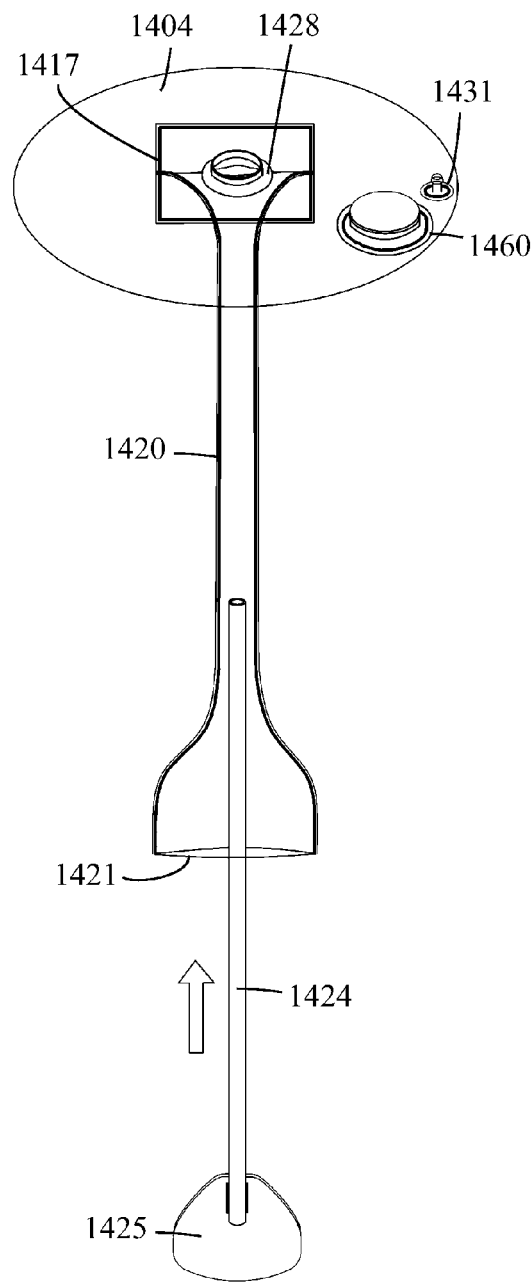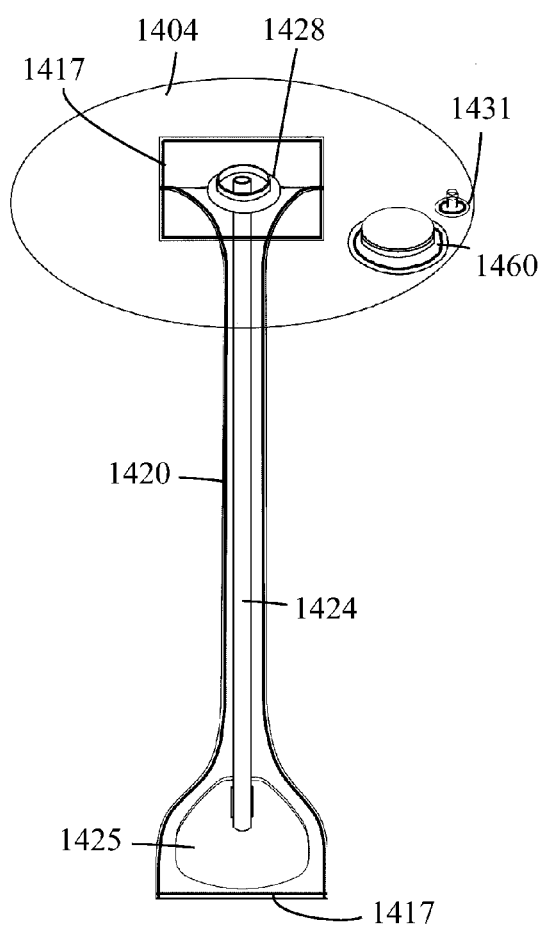
FIG._16C   FIG._16D

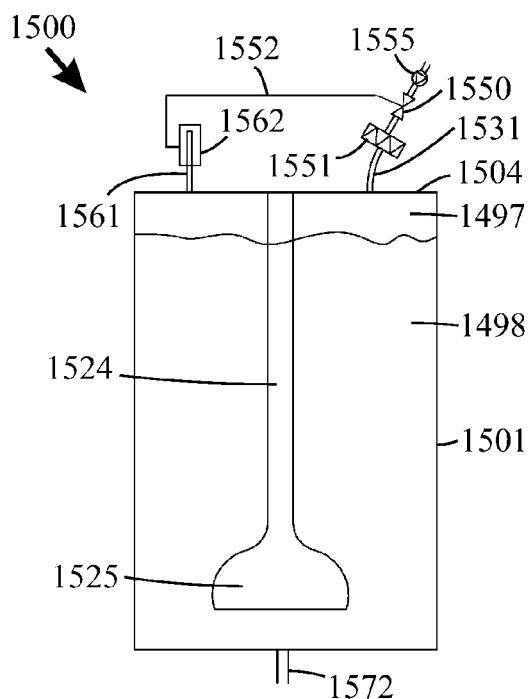
FIG._17A
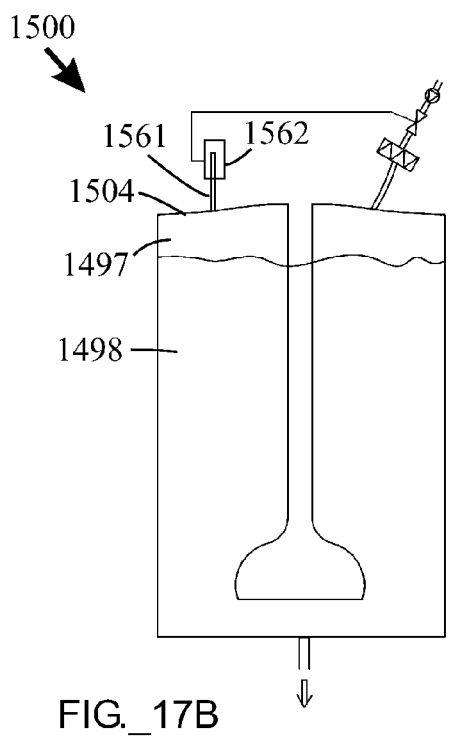
FIG._17B
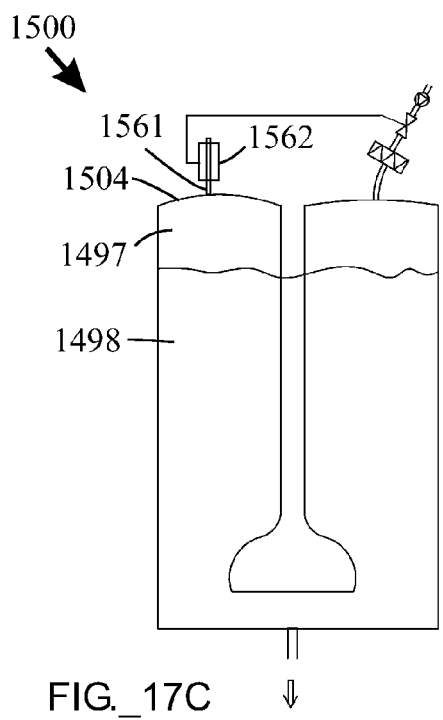
FIG._17C
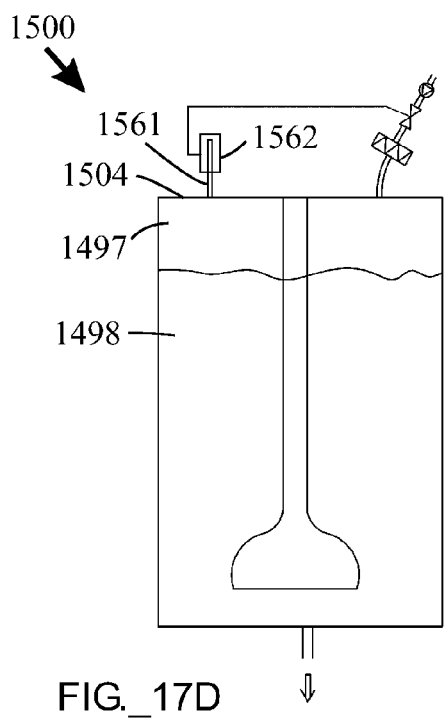
FIG._17D

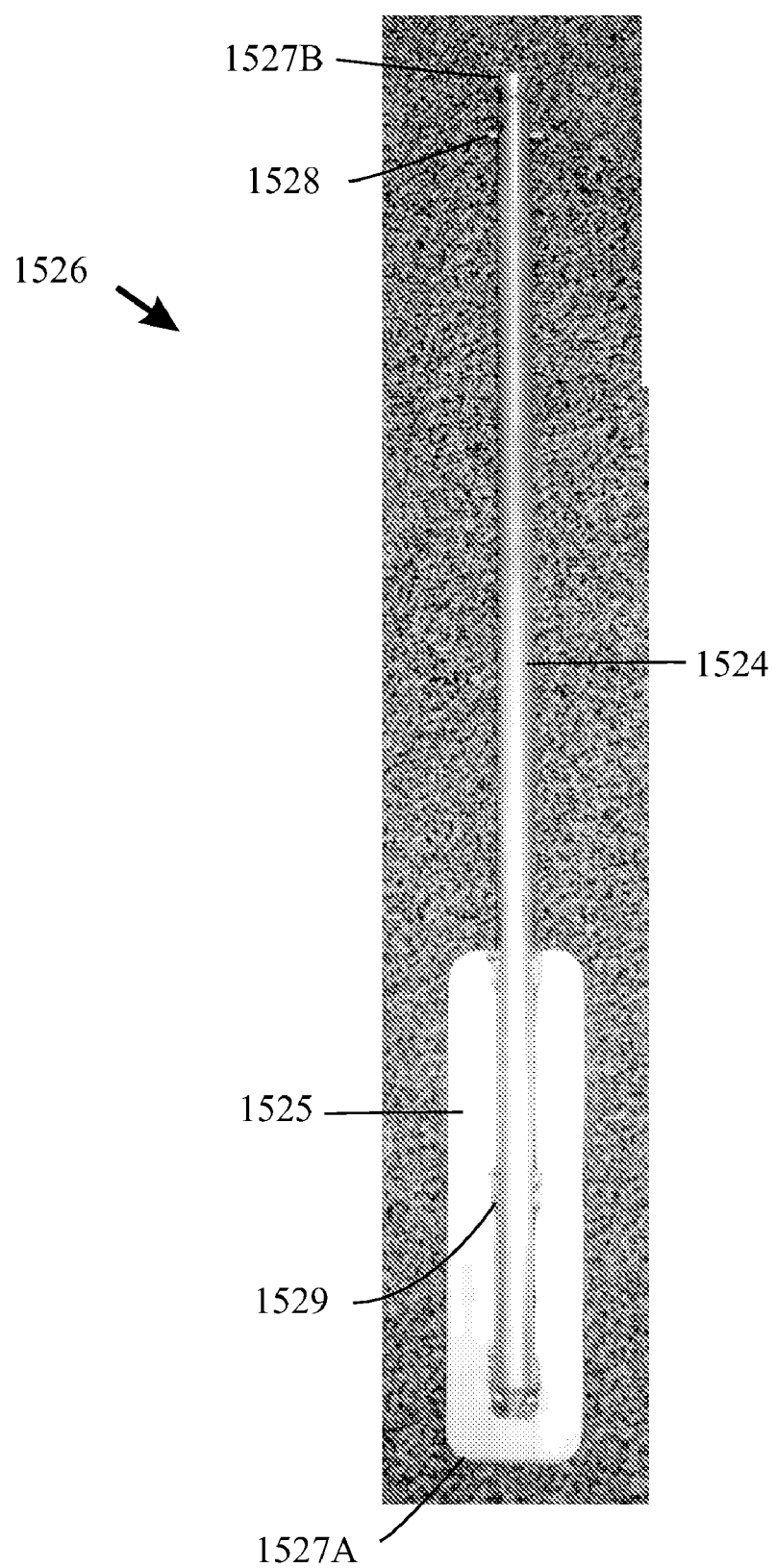
FIG._18

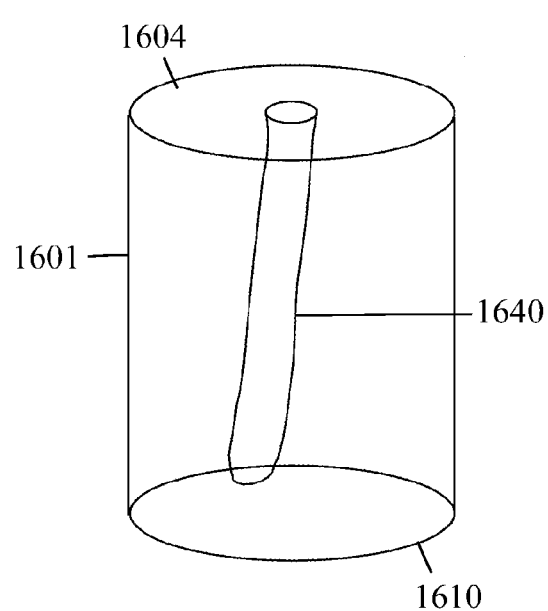
FIG._19A
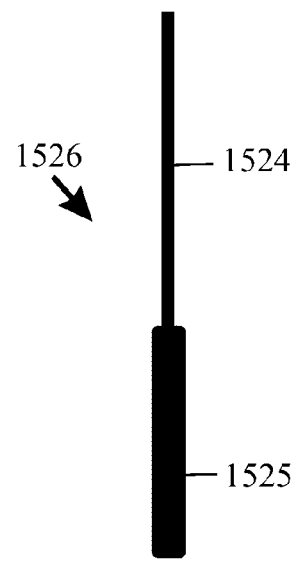
FIG._19B
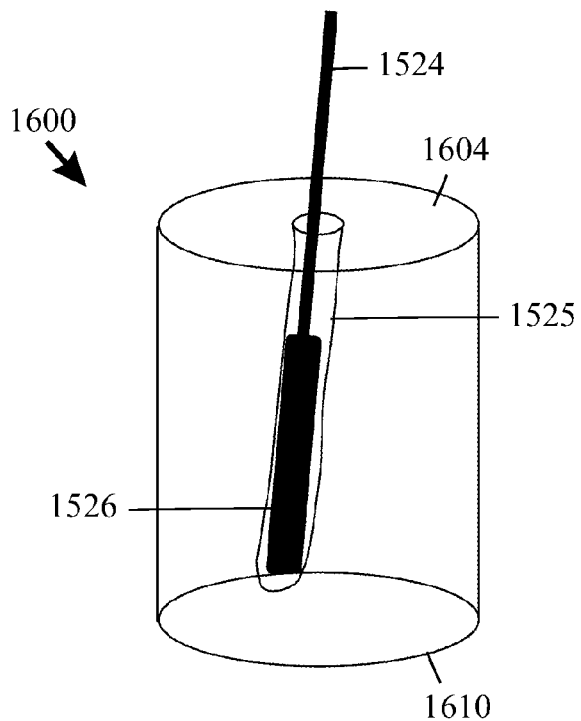
FIG._19C

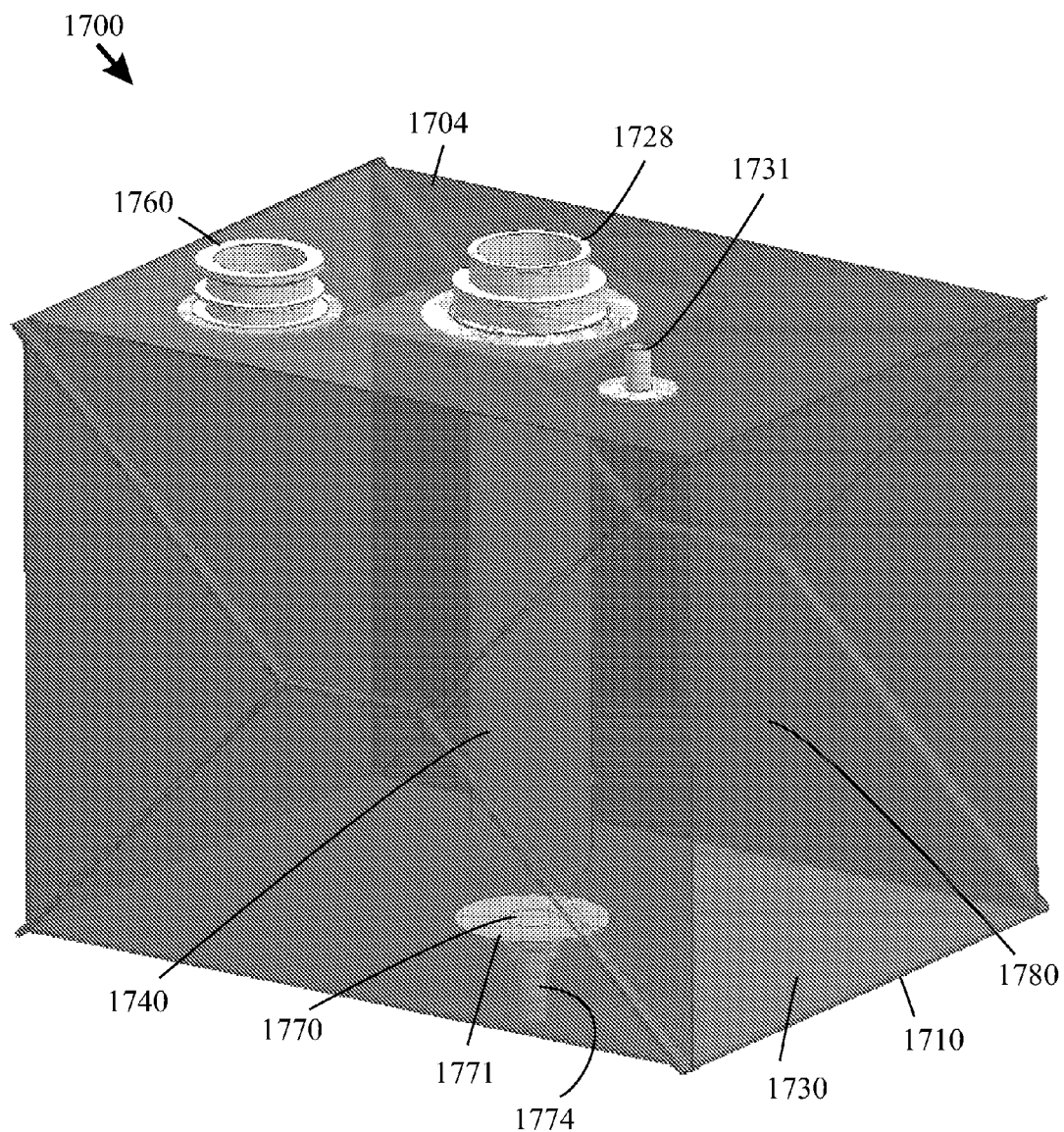
FIG._20

SYSTEMS AND DEVICES FOR MIXING SUBSTANCES AND METHODS OF MAKING SAME

STATEMENT OF RELATED APPLICATION(S)

This present application claims priority under the provisions of 35 U.S.C. §371 of International Application No. PCT/US07/67163 filed Apr. 21, 2007, which in turn claims priority of U.S. Provisional Patent Application No. 60/794,206 filed on Apr. 21, 2006. The disclosures of such international application and U.S. priority application are hereby incorporated herein by reference in their respective entireties, for all purposes.

FIELD OF THE INVENTION

This invention generally relates to mixing of components, and more particularly to systems and methods preferably utilizing flexible bags for industrial mixing of various solids, liquids, gases and combinations thereof.

DESCRIPTION OF THE RELATED ART

The mixing of components, such as different types of solids, liquids and/or gases, has a number of applications in different industries. For example, in the pharmaceutical industry, different types of drugs are mixed together. In the medical field, body fluids (such as blood) and/or drugs are typical components that are mixed. In the semiconductor field, wet solutions are combined with abrasives to make slurries. The food industry also incorporates mixing operations into a number of applications. For example, water is mixed with dehydrated food for the rehydration of such food.

However, in these and other industries, the components that are mixed may be hazardous, dangerous, infectious and/or require high levels of purity. For example, in the pharmaceutical and/or medical industries, the components that are to be mixed may be toxic. Additionally, in a number of situations, the handling of powders may be dangerous because of the possibilities of inhalation of such powders. In the medical field, individuals that handle body fluids, such as fluids that are HIV-infected, do so while attempting to avoid direct contact with these fluids. Furthermore, in the semiconductor industry, handling of chemicals is avoided to reduce the potential for forming particulate and introducing impurities.

Conventional mixing devices generally involve a glass tank for components that are of small volumes and a stainless steel tank for components of larger volumes. These tanks often include a screw to agitate and maintain powders within suspension. Such screws are also used to homogenize multiphase solutions. Prior to use, these mixing tanks must be washed and sterilized. Typically, an autoclave is used for washing and sterilizing small volume tanks, while a water steam-based operation is employed for washing and sterilizing larger volume tanks. When preparing batches of post-etch residue removers for semiconductor applications, introduction of contaminants must be excluded at all levels of processing to decrease particulate formation, which leads to device failure. These wash, sterilize, and process operations, which are essential to the specified technologies, are typically time-consuming and expensive, and require highly qualified individuals for their performance. Further, periodic maintenance of mixing devices associated with the various technologies must be performed to ensure proper operation. In certain cases, washing/sterilizing operations as well as the maintenance of these mixing devices may represent more than a third of the total cost of operating and maintaining such mixing devices, which may be prohibitively expensive for given applications. Additionally, mixing of components may cause the pressure to increase within these conventional mixing devices. If this increased pressure is not accounted for, then the mixing of such components may become dangerous, such as the possibility that the tanks could break apart/explode due to this internal pressure. Moreover, with the use of many mixing devices currently employed to mix pharmaceuticals, the displacement of some pharmaceutical outside the mixing device cannot be eliminated, and therefore the amount of pharmaceutical remaining inside the mixing device, after mixing, may not be sufficiently accurate or precisely known. This is problematic when the FDA requires the administration of such a pharmaceutical in precise, accurate and known quantities.

Due to their multiple advantages, disposable containers are becoming increasingly useful in many industrial applications, particularly as storage containers.

In biological processing, there is an ever-increasing need for disposable products, such as storage bags, which can range in size from 10 to more than 3,000 liters. Current uses include, among others, storage of products or components awaiting disposition to further processing steps such as, for example, purification. Often, however, the stored products or components are mixtures, which, over time, may separate out into phases or components. Emulsions and suspensions, for example, are particularly predisposed to such phase separations.

Current industry standards require remixing, regeneration and/or revalidation of a suspension or emulsion before further processing can resume. In order for remixing to occur without removing the contents from a storage bag, a magnetic stir bar is used. Often, the duration of the regeneration/revalidation step is up to several hours, and the quality of mixing is not uniformly high. Additionally, such a process is prone to particle generation inside the bag that contaminates the formulation therein.

Alternatively, a recirculation loop may be employed to regenerate mixtures, such as emulsions or suspensions, whereby liquid separated from the bulk mixture is repeatedly drained from the foot or base of the storage bag and refilled through the top of the bag. In addition to being time-consuming, such an alternative process requires the container to be opened and resealed.

As noted above, mixing of materials continues to face challenges in many industrial applications. Therefore, systems utilizing disposable elements and providing storage and mixing capabilities are needed. Desirable systems should provide benefits including any of the following: reduced labor requirements, lower production costs, and improved product quality in mixing applications.

Certain solid-liquid and liquid-liquid mixing applications are conventionally performed in open vessels lined with disposable liner materials, with the mixing energy provided by a motor driven (shear) impeller that is reused and typically cleaned between uses. To provide adequate mixing performance, high rotational velocities (e.g., high RPMs) are often used. The utility of such systems is limited because some products cannot handle high shear forces, yet still require high levels of induced turbulence for full dissolution. Additionally, high shear mixing may also cause foaming, which is undesirable in certain applications. There exists a need for improved mixing systems adapted to avoid these shortcomings.

In systems requiring sterile mixing, it may be desirable to provide a closed mixing vessel. As various contents are supplied to and extracted from the mixing vessel, or as various reactions occur within the vessel, the pressure within the vessel may change substantially. Particularly if flexible or collapsible materials are used for the vessel walls, the vessel may expand or contract with these changes in pressure. Taken to an extreme, such volumetric changes may impede movement of the mixing element and thus hinder mixing, or may cause the vessel to rupture. While venting the vessel to atmosphere would eliminate such problems, such ventilation would contaminate the previously sterile environment of the closed container. Alternatively, conventional pressure control systems might appear to present a satisfactory solution, but their implementation may be hindered with disposable mixing vessels such as those constructed with film-based liner materials due to the impracticability of interfacing pressure sensors with such materials.

SUMMARY OF THE INVENTION

The present invention relates to various aspects of mixing systems and methods, each preferably employing a mixing tank comprising flexible bag or film material.

In a first separate aspect, the invention relates to a mixing apparatus comprising: a hollow mixing tank having at least one interior wall bounding an internal volume; a first rod insertion element and a second rod insertion element disposed along at least one surface of the mixing tank; a first mixing paddle adapted to engage a first support rod extending through the first rod insertion element and mechanically coupleable to receive kinetic energy from at least one kinetic energy source, the first mixing paddle having at least one first widened paddle portion that is wider than a nominal diameter or cross-sectional width of the first support rod; a second mixing paddle adapted to engage a second support rod extending through the second rod insertion element and mechanically coupleable to receive kinetic energy from at least one kinetic energy source, the second mixing paddle having at least one second widened paddle portion that is wider than a nominal diameter or cross-sectional width of the second support rod; wherein the first rod insertion element has an associated first sealing portion that inhibits continuous rotation of the first support rod about a longitudinal axis thereof, and the second rod insertion element has an associated second sealing portion that inhibits continuous rotation of the second support rod about a longitudinal axis thereof, with each of the first sealing portion and the second sealing portion serving to isolate the interior volume from a surrounding environment. In one embodiment, each rod insertion element comprises a coupling guide defining an aperture sized to permit pivotal arrangement of a support rod between a kinetic energy source and the tank, and each sealing portion comprises an integral sleeve containing a mixing paddle. In another embodiment, each rod insertion element comprises a reinforcing flange affixed to a support rod, and each sealing portion comprises a non-rotating sealed joint between a flange and the tank. In another embodiment, each rod insertion element comprises a first compression element adapted to compress and sealingly engage a gatherable material portion of the tank around a support rod.

In a second separate aspect, the invention relates to a mixing apparatus comprising: a hollow mixing tank having at least one interior wall bounding an internal volume; a rod insertion element disposed along a surface of the mixing tank; a mixing paddle adapted to engage a support rod extending through the rod insertion element and mechanically coupleable to receive kinetic energy from a kinetic energy source, the mixing paddle having at least one widened paddle portion that is wider than a nominal diameter or cross-sectional width of the support rod; wherein the rod insertion element inhibits continuous rotation of the support rod about a longitudinal axis thereof and serves to isolate the interior volume from a surrounding environment. In various embodiments, the rod insertion element may include a reinforcing flange affixed to the support rod and the tank, or a compression element adapted to compress and sealingly engage a gatherable material portion of the tank around the support rod.

In a third separate aspect, the invention relates to a mixing apparatus comprising: a kinetic energy source; a hollow mixing tank having a substantially central axis and an interior bounded by at least one interior wall; a mixing paddle disposed at least partially within the interior of the mixing tank; a pivot guide operatively disposed between the kinetic energy source and the mixing paddle; and a transfer shaft extending through the pivot guide and adapted to transfer kinetic energy from the kinetic energy source motor to the mixing paddle; wherein the mixing paddle is adapted to travel within the tank through a defined path at a nonzero angle relative to the central axis.

In a fourth separate aspect, the invention relates to a mixing apparatus comprising: a hollow mixing tank having at least one tank wall bounding an internal volume and comprising a flexible tank wall material imparting pressure-dependent variable internal volume character to the mixing tank; a mixing element adapted to move within the internal volume; and a volumetric compensation system adapted to maintain the internal volume of the mixing tank within predetermined limits.

In a fifth separate aspect, the invention relates to a method for fabricating a mixing apparatus utilizing (1) at least a portion of a mixing tank having an interior surface defining a coupling aperture, and (2) a sleeve having a first end defining a first aperture sized to receive a shaft and a second end defining a second aperture sized to receive a mixing paddle, the method comprising: registering the first aperture with the coupling aperture; sealingly welding the sleeve along the first end to the interior surface; inserting a mixing paddle into the second end through the second aperture; and sealingly welding the sleeve along the second end to close the second end and retain the mixing paddle.

In another aspect, any of the foregoing aspects may be combined for additional advantage.

Other aspects, features and embodiments of the invention will be more fully apparent from the ensuing disclosure and appended claims.

BRIEF DESCRIPTION OF THE DRAWINGS

Embodiments of the invention may be best understood by referring to the following description and accompanying drawings, which illustrate such embodiments. In general within the drawings, like numbers are intended to refer to like elements or structures. Reference numbers are the same for those elements that are the same across different Figures. None of the drawings are drawn to scale unless indicated otherwise. In the drawings:

FIG. 1 illustrates a perspective view of a disposable mixing tank, according to one embodiment of the present invention.

FIG. 2 illustrates a perspective view of the substantially parallelepiped shaped mixing tank of FIG. 1.

FIG. 3A illustrates a perspective view, and FIG. 3B illustrates a perspective view of an expanded portion, of the substantially cylindrical sealed sleeve 140 of the mixing tank of FIG. 1.

FIGS. 4A-4C illustrate perspective views of: a disposable mixing tank and mixing means arranged separately; mixing means fully inserted into the disposable mixing tank; and mixing means partially inserted into the disposable mixing tank, respectively, according to a further embodiment of the present invention.

FIG. 5A illustrates a perspective view of sealed sleeve containing a mixing paddle and an exploded view of a mixing paddle and mixing shaft.

FIG. 6 illustrates a side view of a disposable mixing tank and associated sealed sleeve according to a further embodiment of the present invention, with the sealed sleeve shown in various positions of a 360 degree range of motion within the tank.

FIG. 7 illustrates a perspective view of a sealed sleeve-containing disposable mixing tank and mixing means supported by a frame, all according to a further embodiment of the present invention.

FIG. 8 illustrates a flow diagram for the steps of a method for mixing components according to a further embodiment of the invention.

FIG. 9 illustrates a perspective view of an open mixing tank and a conventional axially rotating mixing impeller known in the prior art.

FIG. 10 illustrates a perspective view of an open mixing tank within which a mixing paddle is directed by a shaft to travel within the tank through a defined path at a nonzero angle relative to the central vertical axis.

FIG. 11A illustrates a perspective view of a first motor-driven mixing system including a motor mount, a pivot guide, and a mixing tank having a sealed sleeve surrounding a mixing paddle adapted to move within the tank.

FIG. 11B illustrates an expanded view of a portion of the system of FIG. 11A, showing the sealed sleeve and mixing paddle in various positions of a 360° range of motion within the tank.

FIG. 12A illustrates a perspective view of a second motor-driven mixing system including a motor mount and two motors with associated pivot guides adapted to drive two mixing paddles disposed in sealed sleeves within a single tank.

FIG. 12B illustrates an expanded view of a portion of the system of FIG. 12A, showing the two sealed sleeves and mixing paddles in various positions of a 360° range of motion within the tank.

FIG. 13A illustrates a perspective view of a mixing device including a cylindrical mixing tank having a sleeveless mixing element including an interior paddle and a protruding shaft sealingly engaged to the tank via a reinforcing flange.

FIG. 13B illustrates an expanded perspective view of a portion of the device of FIG. 13A, showing the joint between the sleeveless shaft and the tank including the reinforcing flange.

FIG. 14A illustrates a perspective view of another mixing device including a cylindrical mixing tank having a sleeveless mixing element including an interior paddle and a protruding shaft mating to the tank with a gathered portion of the tank material.

FIG. 14B illustrates an expanded perspective view of a portion of the device of FIG. 14A, showing the joint between the sleeveless shaft and the tank.

FIG. 14C illustrates a perspective view of an optional clamp for use with the mixing device of FIG. 14A.

FIG. 15 illustrates a perspective view of a cylindrical mixing tank with multiple upper (e.g., inlet) connections and a lower (e.g., drain or outlet) connection, the tank and further including a sealed sleeve containing a mixing paddle.

FIG. 16A illustrates a perspective assembly view of a sleeve open at both ends and an aperture-defining top wall of a mixing tank.

FIG. 16B illustrates a perspective view of the assembled sleeve and mixing tank top wall of FIG. 16A, with the open sleeve registered to the aperture and welded to the underside of the mixing tank top wall.

FIG. 16C illustrates a perspective assembly view of the joined sleeve/mixing tank top wall of FIG. 16B with a shaft and mixing paddle being inserted into the open sleeve.

FIG. 16D illustrates a perspective view of the assembled sleeve/mixing tank top wall and shaft and mixing paddle of FIG. 16C following a step of welding the distal end of the sleeve to seal the mixing paddle within the sleeve.

FIGS. 17A-17D illustrate side views of four different states of operation of a mixing apparatus including a vessel comprising a flexible material imparting variable volume character, and including a volumetric compensation system.

FIG. 18 is a photograph of a preferred mixing element including a mixing paddle integrally joined to a shaft having a radially protruding torque transfer pin along its upper end.

FIG. 19A illustrates a perspective schematic view of a mixing tank having a substantially cylindrical sealed sleeve protruding into its interior.

FIG. 19B illustrates a side view of the mixing element of FIG. 18.

FIG. 19C illustrates a perspective view of the mixing element of FIG. 19B inserted into the sealed sleeve of the mixing tank of FIG. 19A.

FIG. 20 illustrates a perspective view of a parallelepiped-shaped mixing tank having multiple upper (e.g., inlet) connections, a lower (e.g., outlet or drain) connection, and a substantially cylindrical sealed sleeve protruding into its interior.

DETAILED DESCRIPTION OF THE INVENTION, AND PREFERRED EMBODIMENTS THEREOF

Figure 4C:
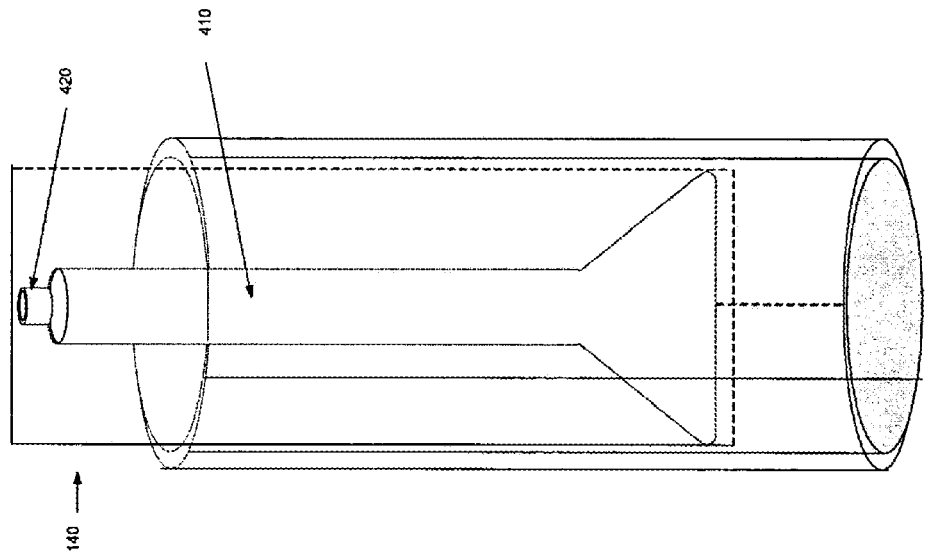

The following patent disclosures applications are hereby incorporated by reference in the present application as if set forth herein: U.S. Patent Application Publication No. 2005/0078552 entitled "Flexible mixing bag for mixing solids, liquids and gases;" and U.S. Patent Application Publication No. 2004/0233779 entitled "Flexible mixing bag for mixing solids, liquids and gases;" both of which are commonly assigned to the assignee of the present application.

The present invention is based on an apparatus, method, and system for mixing solids, liquids and/or gases, having the potential to reduce labor, lower production costs, and improve product quality in mixing applications. It allows disposable bags or tanks to be used to replace permanent mixing tanks in many laboratory and pilot scale operations, thus eliminating cleaning, sterilization, and product contamination concerns.

Embodiments of the invention are described to include a disposable and flexible mixing tank having a sealed sleeve arranged therein. The mixing tank and sleeve may be manufactured from any suitable material. In one embodiment, the mixing tank and sleeve are made of any suitable material having a property where upon removal of an extending force, it is capable of substantially recovering its original size and shape and/or exhibits a significant retractive force. As such, the mixing tank and sleeve may be made of any suitable type of stretchable, collapsible, pliable and/or elastic material. In a preferred embodiment, the disposable mixing tank is manufactured from a fully transparent film to allow for visual inspection of the tank's contents before and after use.

As used herein, the term "collapsible" refers to a material that may fold down into a more compact shape.

As used herein, the term "pliable" refers to a material that is supple or adjustable enough to bend freely without breaking.

As used herein, the term "elastic," or "elastomeric" refers to that property of a material where upon removal of an extending force, it is capable of substantially recovering its original size and shape and/or exhibits a significant retractive force.

As used herein, the term "stretch," or "stretchable" refers to a material that is either elastic or extensible. That is, the material is capable of being extended, deformed, or the like, without breaking, and may or may not significantly retract after removal of an extending force. In an embodiment, the stretchable material can optionally be biaxial stretchable.

As used herein, the term "biaxial stretch" or "biaxial stretchable" refers to a material having stretchability in two directions perpendicular to one another, e.g. stretchability in a machine direction and in a cross machine direction, or in a longitudinal direction (front to back) and a lateral direction (side to side).

The mixing tank and sleeve may be manufactured from any suitable material. Suitable materials include, e.g., films, polymers, thermoplastic polymers, homopolymers, copolymers, block copolymers, graft copolymers, random copolymers, alternating copolymers, terpolymers, metallocene polymers, nonwoven fabric, spunbonded fibers, meltblown fibers, polycellulose fibers, polyester fibers, polyurethane fibers, polyolefin fibers, polyamide fibers, cotton fibers, copolyester fibers, open cell foam, polyurethane, polyvinyl chloride, polyethylene, metals, alloys, fiberglass, glass, plastic (e.g., polyethylene (PE), polypropylene (PP), polyvinyl chloride (PVC), polyethylene terephtalate (PET), polyetheretherketone (PEEK) and polytetrafluoroethylene (PTFE) and polyfluoroalkoxy (PFA) derivates thereof), rubber, and combinations or mixtures thereof.

As used herein, the term "film" refers to a thermoplastic film made using a film extrusion and/or foaming process, such as a cast film or blown film extrusion process. For the purposes of the present invention, the term includes nonporous films as well as microporous films. Films may be vapor permeable or vapor impermeable, and function as liquid barriers under normal use conditions.

As used herein, the term "thermoplastic" refers to uncrosslinked polymers of a thermally sensitive material, which flow under the application of heat or pressure.

As used herein, the term "polymers" includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and atactic symmetries.

As used herein, the term "metallocene polymers" refers to those polymer materials that are produced by the polymerization of at least ethylene using metallocenes or constrained geometry catalysts, a class of organometallic complexes, as catalysts.

As used herein, the terms "nonwoven" and "nonwoven web" refer to fibrous materials and webs of fibrous material, which are formed without the aid of a textile weaving or knitting process.

As used herein, the term "spunbonded fibers" refers to small diameter fibers, which are formed by extruding molten thermoplastic material as filaments from a plurality of fine capillaries of a spinnerette having a circular or other configuration, with the diameter of the extruded filaments then being rapidly reduced.

As used herein, the term "meltblown fiber" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter (the average microfiber diameter is not greater than about 100 microns, for example, having an average diameter of from about 0.5 microns to about 50 microns, more particularly, microfibers may have an average diameter of from about 4 microns to about 40 microns).

References in the specification to "one embodiment", "an embodiment", "an example embodiment", etc., indicate that the embodiment described may include a particular feature, structure, or characteristic, but every embodiment need not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments, whether or not explicitly described.

Embodiments of the invention include features, methods or processes embodied within machine-executable instructions provided by a machine-readable medium. A machine-readable medium includes any mechanism, which provides (i.e., stores and/or transmits) information in a form accessible by a machine (e.g., a computer, a network device, a personal digital assistant, manufacturing tool, any device with a set of one or more processors, etc.). In an exemplary embodiment, a machine-readable medium includes volatile and/or non-volatile media (e.g., read only memory (ROM); random access memory (RAM); magnetic disk storage media; optical storage media; flash memory devices; etc.), as well as electrical, optical, acoustical or other forms of propagated signals (e.g., carrier waves, infrared signals, digital signals, etc.).

Such instructions are utilized to cause a general or special purpose processor, programmed with the instructions, to perform methods or processes of the embodiments of the invention. Alternatively, the features or operations of embodiments of the invention are performed by specific hardware components, which contain hard-wired logic for performing the operations, or by any combination of programmed data processing components and specific hardware components. Embodiments of the invention may be implemented with or include software, data processing hardware, data processing system-implemented methods, and various processing operations, further described herein.

The disposable mixing tank as described herein provides a closed system for use in all phases of processing, reconstitution or revalidation of mixtures. Preferably, the mixing tank is flexible. The mixing tank may be manufactured from pyrogen free, sterile materials, to reduce risks associated with cross contamination. The flexible bag may comprise one or more ports for filling, spiking, adding and/or draining components to reduce the amount of human contact with the various components (which may be hazardous, dangerous and/or infectious) that are to be mixed as part of and during the mixing of such components.

In one embodiment, the present invention provides a disposable and flexible mixing tank having a sealed sleeve arranged therein. As a single-use apparatus, the mixing tank may be used to mix two or more components, and store any of the two or more components before or after mixing. Accordingly, the mixing tank may be discarded after a single use, thereby eliminating washing/sterilizing operations as well as maintenance associated with conventional mixing devices. Moreover, as will be described, in one embodiment, a number of inlet and outlet openings may be further incorporated into the mixing tank FIG. 1 illustrates a perspective view of a disposable mixing tank 100 according to one embodiment of the present invention. The tank is useful for storing and/or mixing liquids, solids, and/or gases. The tank may have a volume of 5 liters or more, and be of a collapsible type that assumes a substantially parallelepiped shape when filled. A support frame 115 may support the mixing tank 100, to maintain a sufficient tension during loading of components into the mixing tank as well as during a mixing step. Mixing tank 100 comprises a bottom wall 110, a top wall 120, and four lateral walls 130. The mixing tank may further comprise inlet(s) 160 and optional outlet(s) 170. In particular, FIG. 1 illustrates a perspective view of a flexible mixing tank (apparatus/device) that includes a sealed sleeve or compartment 140, which is defined by wall 150. The sealed sleeve may be located on or attached to any wall of the mixing tank. Preferably, however, the sealed sleeve is arranged on the upper or top wall and centrally located.

The disposable mixing tank 100 may include any number of inlet openings 160 and outlet opening(s) 170. A more detailed description of the different components of the mixing tank 100 will be described below in conjunction with the description of the various components thereof.

The flexible mixing tank may be manufactured to assume any shape and volume when filled. Preferably, the shape of the mixing tank is cylindrical or parallelepiped and the volume is between 5 and 10,000 liters. More preferably, the volume of the flexible mixing tank is between about 10 and 3000 liters.

FIG. 2 illustrates a perspective view of the substantially parallelepiped shaped mixing tank of FIG. 1. The bottom, top and lateral walls, 110, 120 and 130 respectively, having interior portions, 210, 220 and 230 respectively, and having exterior portions, 211, 221, 231, respectively, may be of any suitable thickness readily determined by one skilled in the art. Moreover, each wall may be manufactured from one or more of the same or different materials. Moreover, each wall may be manufactured from one or more of the same or different materials.

FIGS. 3A and 3B illustrate perspective views of the substantially cylindrical sealed sleeve 140 of the mixing tank of FIG. 1, and an expanded portion thereof, respectively. The wall 150 of sealed sleeve 140, having both an interior portion 351, and an exterior portion 352, respectively, may be manufactured from materials that are the same as or different from the mixing tank walls. When the sleeve 140 of FIG. 3A is joined to the tank 100 of FIG. 2, the interior portions 210, 220, 230 of mixing tank walls 110, 120, 130 and the exterior portion 352 of the sealed sleeve 140 together define an interior volume 180 of mixing tank 100, configured to house components of a mixture, before or after a mixing process.

The sealed sleeve 140 may be of any suitable thickness readily determined by one skilled in the art. Moreover, the sealed sleeve, 140, may comprise multiple sections, such as side wall(s) or a single article of manufacture.

The sleeve 140, which is preferably flexible, is sealably and non-rotatably coupled to the disposable mixing tank 100 at a seam or juncture 190 by any process readily available to one skilled in the art, including, but not limited to, adhesive joining, welding (e.g., RF welding), heat shrinking, shrink down plastic tubing, or combinations thereof. As compared to the use of rotatable mechanical seals employed with conventional axially rotatable mixers, use of an integral sleeve enhances reliability by providing a sealed barrier that eliminating the possibility of leakage or infiltration of contaminants. A sleeve cavity 353 is defined by the interior portion of sleeve wall 351, and has length or height and diameter or width dimensions. The sleeve may be of a regular or irregular shape (i.e., cylindrical vs. tapered, respectively). Moreover, the sleeve may be form fitting so as to directly contact an object arranged therein, much like a hand in a glove. In this regard, the sleeve preferably acts to inhibit continuous rotation of a support rod associated with a mixing paddle about a central longitudinal axis of the support rod. The shape and size of a mixing paddle may be selected to provide the desired mixing utility. A mixing paddle preferably includes a widened paddle portion that is wider than a nominal diameter or cross-sectional width of an associated support rod. Such widened paddle portion may constitute a broad flat paddle face. A paddle may include an integrally or permanently joined shaft portion adapted for coupling with an external kinetic energy source, optionally via an intermediate transfer shaft matable either along the widened paddle portion, or along a shaft portion of the paddle. In one embodiment, a shaft portion of a paddle is hollow, and a transfer shaft is adapted for insertion into the hollow shaft portion.

The sleeve may define a sealed passageway for insertion or arrangement of mixing means therein. The mixing means is isolated from the interior of the mixing tank, by the sleeve wall and hence does not contact the interior of the tank 180 or components therein. The mixing means, which when placed in a mixing mode, serves to mix components in the tank. The mixing means serves to create turbulence and accomplish mixing while presenting no risk of contact with the mixture inside the vessel.

Figure 4B:
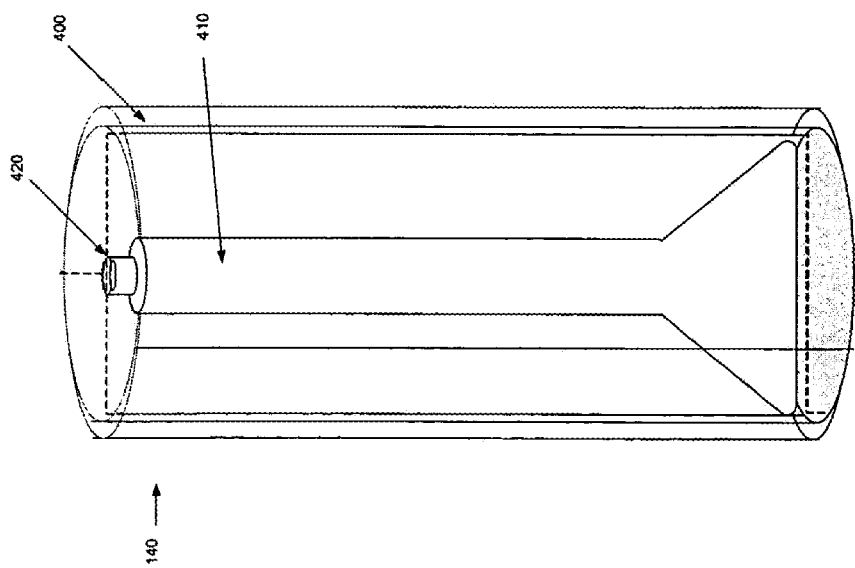

FIGS. 4A-4C illustrate perspective views of a sealed sleeve 140 mixing means 400. As shown by FIG. 4B, the sealed sleeve 140 defines a cavity for arrangement of mixing means 400. According to one embodiment of the present invention, mixing means 400 comprises a mixing paddle 410, with an associated coupling means 420 for coupling to, for example, a shaft of a mixer (not shown).

As used herein, the term "mixing means" relates to a mechanical system or components thereof, capable of transferring energy or motion to the materials housed in the mixing bag. The mixing means, which is isolated from the interior of the mixing tank by the exterior sleeve wall, serves to create turbulence and mixing while presenting no risk of contact with the mixture inside the vessel. Useful mechanical system components readily insertable into the sealed sleeve for transfer of energy to the components may include elements such as, but not limited to, piezoelectric actuators, ultrasonic generators, rotation elements, swaying elements, blending elements, vibration elements, eductors, stirring elements, agitation elements, turbine elements, stator/rotor elements, impellers, helical mixing elements, and vortex generators. The mechanical system may be portable, or fixed mounted. Preferably, a component of the mechanical system comprises a rigid, detachable, support rod or shaft, which is insertable into the sealed sleeve. The support rod or shaft, having a proximal end closest to the upper wall 120 of mixing tank 100 and distal end farthest from upper wall 120 of mixing tank 100, may be enhanced by additional feature(s) such as paddles and/or blades. Moreover, the additional feature(s) such as paddle and/or blade, may be form fitted into the sleeve during a manufacturing process. Paddles of any suitable size and/or shape may be selected for a desired mixing application. In a preferred embodiments, a mixing element comprising a mixing paddle—whether or not disposed within a sealed sleeve—is adapted to travel within a mixing tank through a defined path (e.g., a regular arcuate path) at a nonzero angle relative to a central axis of the tank, without continuous rotation of a support rod associated with the paddle.

Figure 5C:
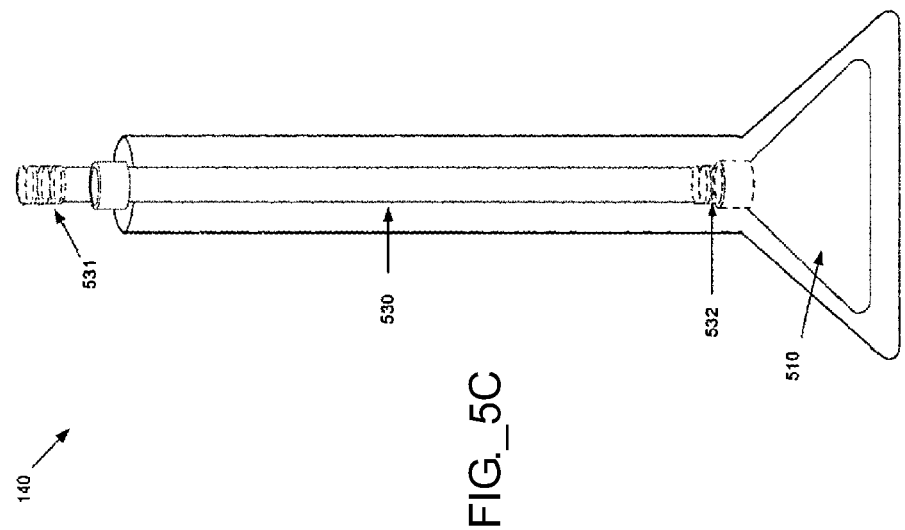
FIG. 5C illustrates the mixing shaft fully inserted into paddle-containing sealed sleeve of FIGS. 5A-5B, all according to a further embodiment of the present invention.
Figure 5B:
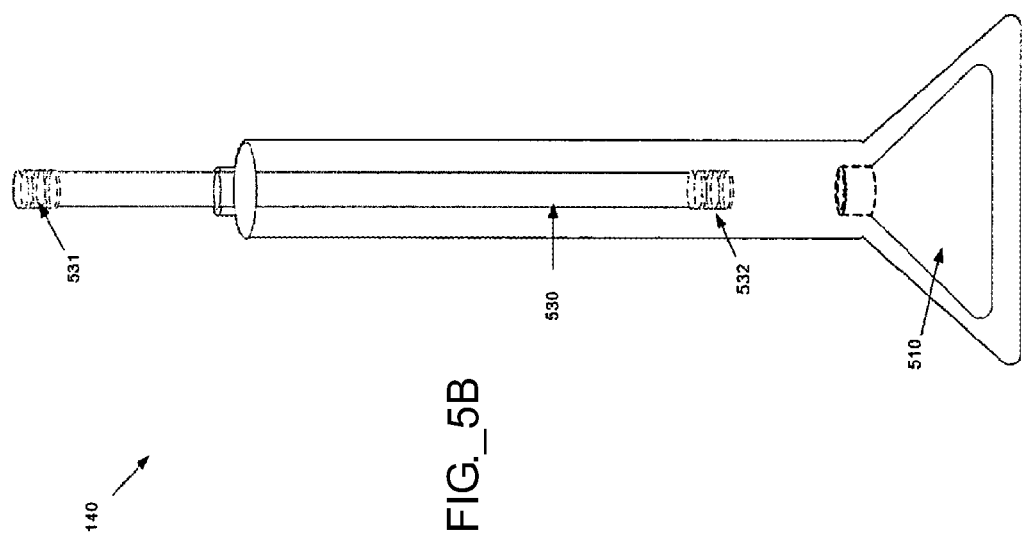
FIG. 5B illustrates the mixing shaft partially inserted into the paddle-containing sealed sleeve of FIG. 5A.

FIGS. 5A-5C illustrate the sealed sleeve 140 of mixing tank 100 and mechanical elements according to a preferred embodiment of the present invention. A sealed sleeve 140 comprises a paddle 510, hollow cavity 520, mixing shaft 530, and coupling guide 540. More specifically, FIG. 5A shows a sealed sleeve 140 having a paddle type device 510 form fitted therein during a manufacturing step. Such form fitted sleeve may serve to inhibit continuous rotation of the shaft 530 around a central longitudinal axis thereof. A hollow cavity 520 in the interior of sealed sleeve 140 provides for arrangement and coupling of a shaft- or rod-type component 530 to the paddle-type device 510. The support rod or shaft 530, having a proximal end 531 closest to the upper wall 120 of mixing tank 100 and distal end 532 farthest from upper wall 120 of mixing tank 100, couples to the paddle 510 at distal end 532. Such coupling may be made by any means readily available to one skilled in the art, at any time prior to a mixing step in a manufacturing process. The proximal end of the support rod 530 may couple to an external kinetic energy source such as, for example, mixer motor driver (not shown). Any coupling suitable for transfer of torque to the support rod may be used, such as, but not limited to, a splined coupling, a keyway coupling, clamped engagement, and the like. The interior of hollow cavity 520 may be defined by the interior wall of the sealed sleeve 140. Alternatively, the interior of hollow cavity 520 may be defined by a separate integrated sleeve to provide additional protection and/or guard against potential punctures from a misfed or faulty rod or shaft. A coupling guide 540, which may or may not be sealed to the sleeve 140, serves as a rigid guide for insertion, arrangement and coupling of the support rod or shaft 530. The coupling guide defines an aperture for receiving the support rod. Such aperture is preferably sized to permit pivotal arrangement of the support rod between an external kinetic energy source (e.g., a motor) and the mixing tank. The paddle-type device 510, support rod or shaft 530, and coupling guide 540 are preferably rigid, and may be formed from any material readily available to one skilled in the art, including, but not limited to, metals, alloys, composites, ceramics, composition(s) and material(s) described herein, and/or mixtures thereof. Preferably, the paddle device is absent of any sharp edges.

FIG. 5B shows insertion of a support rod 530 through a coupling guide 540 and into hollow cavity 520, while FIG. 5C shows the support rod 530 coupled to the paddle 510.

Preferably, the sealed sleeve is capable of a range of motion similar to an arm and hand in the glove of a glove or dry box. In a conventional dry box, the glove, which is preferably form fitted to the user's arm and hand, couples to the wall of the dry box, and isolates a user from an interior environment of the box. Although a portion of the glove contacts the contents in the box, the user is isolated from contacting the contents of the box by the glove, while a wide range of mobility is provided to the user's arm(s) and hand(s).

FIG. 6 serves to illustrate, in 2-dimensions, mixing tank, 100, and sealed sleeve 140, having a paddle, 600, arranged therein, by a form-fitting means. The paddle may include one or more sections of manufacture. The interior portions of bottom, top, and lateral walls, 210, 220 and 230 respectively, and exterior portion of sealed sleeve wall, 352, serve to define the interior volume, 180, of mixing tank 100, for housing components of a mixture, before or after a mixing process. Sealed sleeve, 140, comprising paddle 600, moves within mixing tank 100 at a nonzero angle A relative to a central vertical axis 375 of the tank 100, though a 360 degree range of motion (represented by dashed line 360) in a plane parallel to the mixing tank base 110, whereby through mechanical motion, the paddle 600 at least partially combines the components housed therein.

In one embodiment, the disposable mixing tank may be used for containment and storage of at least one component of the mixture, whereby the disposable mixing tank may store at least a first component for a period of time until at least a second component is added to the mixing tank for subsequent combining and mixing with the at least first component. Any of the first and second components may comprise multiple compositions as in a mixture or blend, or the first and second components may consist essentially of single compositions. Each component may be introduced into the mixing tank by one or more inlet openings.

In a still further embodiment, the present invention relates to a method of remixing, regenerating and/or revalidating a mixture, which over time has separated into two or more phases or components. The mixture, having been stored in a disposable mixing tank having a sealed sleeve therein, comprises two or more components prone to phase separations, including but not limited to emulsions, blends and suspensions (e.g., biological solutions comprising plasma, red cells, viruses, etc., or CMP slurries used in semiconductor manufacturing processes). The sleeve defines a sealed passageway for insertion or arrangement of mixing means therein. When the sleeve and mixing means are placed in a mixing mode, they serve to remix, regenerate, and/or revalidate the mixture in the mixing tank. Advantageously, the present invention serves to reduce the time required to regenerate a mixture because there is no downtime due to revalidation, as no transfer of materials is required.

In a further embodiment, the present invention relates to a kit including a disposable and collapsible tank having a sealed and collapsible sleeve disposed therein. The collapsible tank, having a storage/containment area defined by an interior wall of the collapsible tank and an exterior wall of the sleeve, is configured to house components prior to, during, and/or after a mixing process. The collapsible sleeve defines a sealed passageway for insertion or arrangement of mixing means therein. The mixing means is isolated from the interior of the mixing tank by the exterior sleeve wall, and hence does not contact the interior of the tank or components therein. The mixing means, when placed in a mixing mode, serves to mix components within the mixing tank. Preferably, the flexible sleeve includes a mixing rod shaft or other mixing components prearranged therein during a manufacturing process. The kit may further include packaging material and instructions or indicia located on the packaging material or inside the packaging material, and may optionally include ancillary components such as couplers, connectors and filters.

The figures shown herein thus far illustrate various embodiments of the disposable mixing tank in accordance with embodiments of the invention. However, it should be understood that the invention could be performed by embodiments of systems and apparatus other than those discussed with reference to the figures, and embodiments discussed with reference to the systems/apparatus could perform operations different than those discussed with reference to the figures.

A more detailed description of the different components of the disposable and flexible mixing tank 100 of FIG. 1 will now be described.

The tank walls 110, 120, 130 and sleeve walls 150 may be any type of flexible material for providing a flexible mixing apparatus (e.g., different types of plastics). For example, the walls 110, 120, 130, 150 may comprise heat-welded plastic films. In one embodiment, the walls 110, 120, 130, 150 are plastic films with a thickness in range of 5 microns to 500 microns (depending on the type of application). While the walls 110, 120, 130, 150 may be made from a number of different plastics, in one embodiment, the walls 110, 120, 130, 150 are made from a plastic that includes at least one material from the following group: polyethylene (PE), polypropylene (PP), polyvinyl chloride (PVC), polyethylene terephtalate (PET), polyetheretherketone (PEEK) polytetrafluoroethylene (PTFE) and polyfluoroalkoxy (PFA) derivates thereof. In a preferred embodiment, the mixing tank walls are manufactured from materials including at least one of ethylene vinyl acetate and metallocene polyethylene. In another embodiment, the walls 110, 120, 130, 150 comprise a stretchable material, having a deformation of less than approximately five percent when subjected to a tensile force of 100 gmf per inch (per 2.54 cm) of width. The tank and sleeve walls 110, 120, 130, 150 define the storage and/or mixing compartment that isolates components therein from the outside medium/environment. The films 110, 120, 130, 150 preferably also have a mechanical resistance such that the disposable mixing tank 100 may be used under pressure from the outside medium/environment. Preferably, the walls of the disposable mixing tank and sleeve are manufactured from similar materials, having similar thicknesses. In a preferred embodiment the wall thickness of each of the walls of the mixing tank and sleeve is about 200 microns.

In a further embodiment, the mixing tank walls 110, 120, 130 are substantially clear to allow for the viewing of the components and the mixture thereof, such that one skilled in the art may determine when the mix operation is complete based on viewing of the components. In one embodiment, the mixing tank walls include volumetric indicia for measuring the volume of the components therein.

In another embodiment, the disposable mixing tank 100 is a single-use apparatus. In particular, the mixing tank 100 is used to mix, at least partially, components contained therein. More preferably, the mixing tank is used to at least partially mix and store components therein. The result of the mixing of the components may be removed from the mixing tank 100 (as described in more detail below). Thereafter, the mixing tank 100 is discarded. Accordingly, there is no need to wash/sterilize the mixing tank 100 in preparation for subsequent uses. Moreover, because the mixing tank 100 is a single-use apparatus, the mixing tank 100 does not have the ongoing maintenance costs associated with conventional mixing devices. The at least one outlet opening, 170, allows for draining the contents of the disposable mixing tank 100. While the mixing tank 100 is illustrated with separate inlet(s) 160 and outlet(s) 170, embodiments of the invention are not so limited. For example, in an embodiment, a single opening could be used for both loading and draining of components and/or mixtures.

In one embodiment, the inlet opening(s) 160, and the outlet opening(s) 170 include a base plate welded onto the internal or external face of the mixing tank walls 120, 130, such that one end of the opening emerges inside the wall 120, 130 and the other end emerges outside the wall 120, 130. Furthermore, the inlet openings 160 and the outlet openings 170 may be closed using a number of devices, such as tight plugs. In one embodiment, the diameters of the inlet openings 160 and the outlet openings 170 is dependent on the flow rate that a particular component is to be introduced into the mixing tank 100, and/or the admix operation that is to occur by movement of the mixing device arranged in the sealed sleeve 140. For a gas component, the gas inlet and outlet rate (or pressure) may be such that there is a sufficient homogenization of the components in the disposable mixing tank 100.

In a further embodiment, inlet opening(s) 160 and outlet opening(s) 170 may be used to introduce different types of probes into the mixing tank 100. For example, pH, pO2, temperature or pressure probes can be introduced into the mixing tank 100 through a number of inlet 160 and/or outlet 170 openings to check the status of the components and/or the result of the mixing of such components within the mixing tank 100.

The components to be stored in and the components that are to be admixed (mixed), at least partially together, during motion of the mixing device inside the flexible sleeve 140, may be in different phases (different types of solids, liquids and/or gases). For example, the solid components may be different types of powders. The liquid components may be in different organic phases and/or aqueous phases. The gases may include oxygen, air, nitrogen, argon, carbon dioxide, etc. In one embodiment, the components are substantially homogenized. Moreover, the different components may or may not be soluble in reference to each other.

Any of a number of combinations of different components in different phases can be admixed in accordance with embodiments of the invention. For example, a first component in a solid phase may be mixed with a second component in a solid phase. A first component in a solid phase may be mixed with a second component in a liquid phase. In one such embodiment, a powder is suspended in a liquid component when the powder may be partially or totally insoluble in the liquid component. In an embodiment wherein the powder is totally soluble, the operation of the mixing tank 100 is such that the result is a homogenized solution of the powder and the liquid.

Further, a first component in a liquid phase may be mixed with a second component in a liquid phase. In one embodiment, the first liquid component may be partially soluble, totally soluble or totally insoluble with reference to the second liquid component. If at least one liquid component is at least partially insoluble in at least another liquid component, an emulsion is obtained after the mixing/stirring of the mixing tank 100. In an embodiment, if the liquid components are soluble in reference to each other, the operation of the mixing tank 100 is such that the result is a homogenized solution of the two different liquid components.

A first component in a liquid phase may be mixed with a second component in a gas phase. The gas may be inert or may react with at least one component of the liquid component. For example, a gas (that is relatively reactive under the desired conditions) may be oxygen or carbon dioxide when culturing cells or microorganisms or to provide for an oxidation reaction.

The width/diameter of sealed sleeve 140, and the width/diameter of the inlet(s) 160 and outlet(s) 170, are dependent on the size of the mixing tank 100 and on the identity of the components to be mixed and/or transferred. The width/diameter and height of sealed sleeve 140 must allow for the arrangement of mixing means therein. Moreover, the dimensions of the sealed sleeve 140 are based on the size of the mixing tank 100 and the physical characteristics of the components to be mixed. Examples of the type of characteristics on which the diameter of the sleeve 140 is dependent include viscosity, granulometry, density, thixotropy and rheoscopy.

In one embodiment, the mixing tank 100 also includes at least one valve to allow for a release mechanism in the event that pressure builds up within the mixing tank 100 because of the mixing/rotation operation.

In a further embodiment, the disposable mixing tank 100 may comprise a support frame 115, as shown in FIG. 1. The support frame may surround the disposable mixing tank 100 and can couple to the mixing bag 100, through one of a number of connection apparatus (e.g., a clip, a hook, etc., not shown). The frame may additionally function as support for mixing means and related ancillaries. Accordingly, the support frame supports the mixing tank 100, so as to maintain a sufficient tension during loading of components into the mixing tank as well as during the mixing of the components contained therein.

FIG. 7 illustrates disposable mixing tank 100, comprising mixing means 700, whereby both mixing tank 100 and mixing means 700 are supported by a frame 115. Motor-wheel driver 710 couples to rotation wheel 720, which couples to mixing stick 730 through bearings 740, 750. Such bearings 740, 750 enable the mixing stick 730 to be driven by way of a pivotal link through an arcuate (e.g., circular) path in the internal volume of the mixing tank 100 without continuous rotation of the mixing stick about its own longitudinal axis. Movement of the mixing stick 730 is preferably at a nonzero angle relative to a central axis of the tank to sweep along a conical shape. The motor-wheel driver 710 may communicate directly with a processor to execute machine-readable instructions for controlling the movement of the mixing stick 730, including the number of turns along the path, the rate of arcuate movement, the angle of departure from a central axis, and how far to sweep the mixing stick along a particular arc, as described in more detail below in conjunction with the description of the flow diagram 800 of FIG. 8.

In a further embodiment, the disposable mixing tank of the present invention may further comprise a secondary containment system for containment of materials, which may inadvertently leak from the tank during storage, processing, and/or transfer of such materials into and/or out of the mixing tank. The secondary containment system may be fixed or portable. Further, the appropriate secondary containment system for use with the disposable mixing tank may be readily determined by one skilled in the art.

In a further embodiment, the disposable mixing tank of the present invention may further comprise external heating and/or cooling means for controlling the temperature of components in the disposable mixing tank. The secondary containment system may serve as housing for a fluid that conducts heat into or out of the disposable mixing tank, such as with heating and cooling baths. Alternatively, the heating and/or cooling means may envelope the exterior of the disposable mixing tank or a portion thereof as in, for example, heating jackets, heating and cooling tanks, heat exchangers, chillers, and fluid cooling systems. As a still further alternative, the mixing tank may comprise a liner, exterior to the outer walls of sealed cavity 140 and mixing tank 100. The liner preferably envelops at least a portion of the mixing tank and provides a sealed gap or space between the liner and exterior walls of sealed cavity 140 and mixing tank 100. The gap or space is useful for containing fluids having heat and/or cooling capacities. Preferably, the heating and/or cooling fluid contained therein is circulatable in the gap or space by circulation means.

FIG. 8 illustrates a flow diagram for the steps of a method for mixing components, according to a further embodiment of the invention. In a first step described in block 802, components are loaded into mixing tank 100 through an inlet 160. The inlet 160, or multiple inlets (not shown), may be opened in an order that is in accord with a mixing protocol for the components to be loaded into mixing tank 100. For example, a more homogenous solution may be derived for three components if a first component and a second component are mixed, followed by the mixing of the third component into the mixture of the first component and the second component.

In the first step described in block 802, the components may be loaded simultaneously or based on a mixing protocol or instructions from a CPU. As described above, the number of inlet openings 160 allow for the introduction of components ("raw materials" or "reactants") to be mixed within the mixing tank 100. Control continues at a second step described in block 804.

The loading operation as described in the first block 802, while described such that the operations of the second block 804 are subsequent to the operations of the block 802, is not so limited in all embodiments. For example, as described above, different inlets may be opened at different times during the mixing of the components in order to follow a mix protocol for a given set of components. Accordingly, the opening of an inlet for filling may follow a first mix operation, which is followed by a second mix operation.

In a second step described in a second block 804, the components loaded into the mixing tank 100, are mixed, at least partially, based on rotation or other motion of the mixing device as shown in FIG. 7. The mixing of the components may be performed or controlled by an individual and/or a control apparatus (not shown). The mixing of the components may be carried out by a number of rotations of the mixing means 700, wherein one rotation includes rotating at least a 360 degree turn. In one embodiment, the range of motion through the 360 degree rotation is in the plane parallel to the mixing tank base 110.

In an embodiment to generate a homogenous solution, the rotation of mixing means 700 in the mixing tank 100 continues until the components are approximately homogenized. In an embodiment that includes mixing a liquid and a powder that is at least partially insoluble, the rotation of mixing means 700 continues until the powder is suspended in the liquid.

Moreover, as described above, a number of open passage operations and mix operations may occur in order to follow a given mix protocol. Accordingly, a number of mix operations may occur until the different components are mixed, at least partially, into the final resulting component. Control continues with a third step described in a third block 806.

In a third step described in the third block 806, the at least partially mixed components are drained from the mixing tank 100. In one embodiment, the mixing tank 100 is positioned such that when a plug type device is removed or a valve is opened, mixed components drain from an outlet 170. The drain operation may be facilitated as desired. For example, when the component is a viscous solution having a slow flow, the drain operation may be facilitated through a number of operations. In one embodiment, the drain operation is facilitated by an increase in pressure initiated by introducing a gas into an inlet opening(s) 160. Control continues with a fourth step described in a fourth block 808.

In the fourth step described in the fourth block 808, the mixing tank 100 is discarded. In particular, the mixing tank 100 is discarded after a single use. Accordingly, the washing/sterilizing operations as well as the maintenance associated with conventional mixing devices are not needed. Moreover, as described, embodiments of the invention reduce the amount of human contact with the components (which may be hazardous, dangerous and/or infectious) that are to be mixed as part of and during the mixing of such components.

Another aspect of the invention is directed to a mixing apparatus for open liner mixing bags. As mentioned previously, certain mixing applications are conventionally formed in open vessels with the mixing energy provided by a motor driven impeller. FIG. 9 is representative of such a conventional system 760 in which a tank 765 having a bottom 763 and a lined internal surface 766 (e.g., bearing a film-based or equivalent disposable liner) receives a shear impeller 762 driven by a shaft 761 and motor (not shown). This conventional system 760 requires high rotational velocity to provide adequate mixing performance in many applications. This can be problematic with components that cannot handle high shear forces and/or in applications in which foaming cannot be tolerated.

Referring to FIG. 10, a paddle-based mixing system 770 is suitable for use with an open tank 775 having a lined internal surface 776 and a bottom 773. Rather than employing a sheer impeller 762, the system 770 utilizes a paddle 772 adapted to travel within the tank 775 through a substantially circular path at a nonzero angle relative to a central vertical axis of the tank 775. To help visualize this phenomenon, the travel of the shaft 771 forms a conical (or open semi-conical, depending on the tank diameter) shape through its path. Such a path causes the paddle 772 to sweep through a substantial area of the tank 775, resulting in turbulent mixing without causing the high shear forces generated by a fast-rotating shear impeller.

Referring to FIGS. 11A-11B, a detailed implementation of a mixing system 900 according to one embodiment including a closed tank 901 is shown. The tank 901, which is generally cylindrical in shape, has a top wall 904 defining a substance inlet 960 and access ports 980, 985, and has a bottom wall 903 defining an outlet or drain 970. The tank 901 further includes a sealed sleeve 940 joined to the tank 901 along a reinforced coupling guide 905. The sealed sleeve 940 contains a mixing paddle 910 that is joined to a hollow shaft 930. Adjacent to the coupling guide 905 is a pivot guide 815 (e.g., having a perforated pivot ball) through which a transfer shaft 830 extends to engage (e.g., by insertion) the hollow shaft 930 disposed below. The transfer shaft 830 is linked to a radially offset coupling 812 that engages the output shaft 811 of a motor 899. Preferably, the coupling 812 includes a bearing or other rotation means to permit the shafts 830, 940 not to rotate about their own axes despite being driven through a substantially circular path at a nonzero angle relative to a central vertical axis of the mixing tank 901. Such movement without axial rotation of the shafts 830, 930 ensures that the sleeve 940, which is sealed (e.g., welded) to the tank 901, does not twist, tear, or bind the paddle 910. The motor 899 is supported by a support frame 808, with an extension 809 thereof further supporting the pivot guide 815. Preferably, the support frame 808 further engages the mixing tank 901 to ensure correct positioning between the motor 899, the transfer shaft 830, and the contents of the sleeve 940.

FIG. 11B shows the sealed sleeve 940 and mixing paddle 910 in various positions of a 360° range of motion within the tank 901. The mixing paddle 910 travels in a large, substantially circular path 913 in a plane parallel to the bottom surface 903 or base of the mixing tank 901. Simultaneously, the upper end of the transfer shaft 830 travels in a small, substantially circular path 813 in a similarly parallel plane, but disposed above the pivot guide 815. The travel diameter of the paddle 910 may be modified by adjusting the width of the offset coupling 812, the lengths of the transfer shaft 830 and the hollow shaft 930, and the placement of the pivot guide 815 relative to the shafts 830, 930.

Referring to FIGS. 12A-12B, a mixing system 900A according to one embodiment includes multiple shafts 940A, 940B each having at least one associated mixing paddle 910A, 910B adapted to move within a common closed tank 901A. A benefit of using multiple mixing paddles 910A, 910B is that they can promote uniform mixing in very large volume tanks. The tank 901A, which is generally parallelepiped-shaped, has a top wall 904A defining a substance inlet 960A and access ports 980A, 985A, and has a bottom wall 903A defining an outlet or drain 970A. The tank 901A further includes two sealed sleeves 940A, 940B joined to the tank 901A along reinforced coupling guides 905A, 905B. Each sealed sleeve 940A, 940B contains a mixing paddle 910A, 910B joined to a hollow shaft 930A, 930B. Adjacent to each coupling guide 905A, 905B is a pivot guide 815A, 815B (e.g., having a perforated pivot ball) through which a transfer shafts 830A, 830B extend to engage (e.g., by insertion) the hollow shafts 930A, 930B disposed below. (While hollow shafts 930A, 930B, separate transfer shafts 830A, 830B, and bottom-insert or pre-sealed mixing paddles 810A, 910B are shown, unitary shafts and/or top-insert mixing paddles may be used if desired.) Each transfer shaft 830A, 830B is linked to a radially offset coupling 812A, 812B that engages the output shaft 811A, 811B of a motor 899A, 899B. While two motors 899A, 899B are shown and represent a preferred embodiment, one motor could be used in combination with a gearset or other appropriate linkage (not shown) to drive two or more paddles if desired. Each motor 899A, 899B is supported by a support frame 808A, with extensions 809A, 809B thereof further supporting the pivot guides 815A, 815B. Preferably, the support frame 808A further engages the mixing tank 901A to ensure correct positioning between the motors 899A, 899B, the transfer shafts 830A, 830B and the contents of the sleeves 940A-940B.

FIG. 12B shows the sealed sleeves 940A, 940B and mixing paddles 910A, 910B in various positions of a 360° range of motion within the tank 901A. The mixing paddles 910A, 910B travel in large, substantially circular paths 913A, 913B in a plane parallel to the bottom surface 903A or base of the mixing tank 901A. Simultaneously, the upper end of each transfer shaft 830A, 830B travels in a small, substantially circular path 813A, 813B in a similarly parallel plane, but disposed above the pivot guides 815A, 8915B. The travel diameter of the paddles 910A, 910B may be modified by adjusting the width of the offset couplings 812A, 812B, the lengths of the transfer shafts 830A, 830B, and the hollow shafts 930A, 930B, and the placement of the pivot guides 815A, 815B relative to the shafts 830A, 830B, 930A, 930B. The two paddles are adapted to travel simultaneously within the tank. The paddles may be driven in the same rotational direction, or in opposite directions of rotation. While FIGS. 12A-12B illustrate two shafts 940A, 940B as being operatively coupled to the tank 901A through the top wall 904A, it is to be understood that either or both of such shafts 940A, 940B could be coupled through the bottom wall 903A or any of the side walls. More than two shafts may be employed if desired. Moreover, multiple shafts may be driven (e.g., via gears, belts, or any suitable torque transfer mechanism) via a common kinetic energy source, such as a motor, servo, piston, or the like.

In another embodiment shown in FIGS. 13A-13B, a mixing system 1001 includes a mixing paddle 1010 and sleeveless shaft 1030 for use in a substantially sealed mixing tank 1001. The shaft 1030 is sealed to the tank 1001, whether permanently or removably. At least one wall of the tank 1001 preferably comprises a flexible material such as a polymeric film. Permanent joining between the shaft 1030 and tank 1001 may be performed by solvent welding or thermal welding (e.g., if the shaft comprises a polymeric material) along a joint 1009 or any other appropriate joining means. Removable joining between the shaft 1030 and tank 1001 may be performed, for example, using an optional clamp 1107 (such as illustrated in FIG. 14C).

A reinforcing flange 1006 is provided along the top wall 1004 of the tank 1001 to receive the shaft 1030 and permit the establishment of the joint 1009, such as with a flat circular weld joint 1009. The flange 1006, which may be injection molded with the shaft 1030, is preferably welded to the top wall 1004 as well. Following establishment of the joint 1009, an upper portion 1030A of the shaft 1030 protrudes upward from the tank 1001 to mate with an appropriate mixing mechanism such as shown in FIGS. 12A-12B to move the mixing paddle 1040 within the tank. Since the joint 1009 is rigid, it does not permit the shaft 1030 to rotate about its own axis 1030X (such as described in connection with the system 900 illustrated in FIGS. 11A-11B). Instead, the shaft 1030 is permitted to move within the tank through a substantially circular path at a nonzero angle relative to a central vertical axis of the tank 1001. The paddle 1040 is preferably permanently joined (e.g., by welding) to the shaft 1030 along a joint 1011; alternatively, the paddle 1040 and shaft 1030 may be integrally formed together such as with an injection molding process. The paddle 1040 and shaft 1030 preferably permanently joined to the tank 1001 and manufactured as a single unit and pre-sterilized to that the assembly 1000 is adapted for economical single use (e.g., through the use of low-cost polymeric materials) and subsequent disposal. Alternatively, other suitable materials may be used and the assembly 1000 may be cleaned and/or sterilized between uses if desired.

In one embodiment, at least one wall of the tank 1001 comprises a polymeric film that is preferably substantially optically transmissive or transparent, and the shaft 1030 comprises a polymer adapted to be joined to the top wall 1004 by solvent and/or thermal welding. If desired, a substantially open external frame (not shown) may be provided to support the tank 1001 with associated hooks or connectors (not shown). The upper wall 1004 of the tank 1001 further defines a substance inlet port 1060 and additional apertures 1031, 1032 such as may also be used to admit or extract substances to or from the tank 1001. Each aperture or port 1031, 1032 preferably has an associated supply line 1033, 1034, sealing element 1035, 1036, and coupling element 1037, 1038. The lower wall 1003 of the tank 1001 defines an outlet aperture or port 1072 preferably having an associated drain or outlet line 1074, sealing element 1076, and coupling element 1078. In this manner, the tank 1001 may be joined to other elements of a processing system (not shown), and substances exchanged therebetween may be processed.

FIGS. 14A-14B illustrate another mixing assembly 1100 having a sleeveless shaft 1130 and mixing paddle 1140. The primary distinction between the assembly 1100 and the prior assembly 1000 illustrated in FIGS. 13A-13B is the connection between the top wall 1104 of the tank 1101 and the shaft 1130. In the present assembly 1100, the shaft 1130 is coupled directly to the top wall 1104 without an interposing reinforcing flange 1006 (as shown in FIGS. 13A-13B). The top wall 1104 preferably comprises a flexible material such as polymeric film. The top wall material may be gathered around the shaft 1130 as shown in FIGS. 14A-14B and then welded (e.g., circumferentially welded to the shaft) to form a joint 1119, or optionally clamped using a clamp 1107 as illustrated in FIG. 14C to permit removable engagement between the shaft 1130 and the tank 1101. As before, the shaft 1130 includes a protruding upper portion 1130A and an axis 1130X. Since the joint 1119 is rigid, it does not permit the shaft 1130 to rotate about its own axis 1130X. The mixing paddle 1140 is preferably permanently joined to the shaft 1130 along a joint 1111.

The upper wall 1104 of the tank 1101 further defines a substance inlet port 1160 and additional apertures 1131, 1132 such as may also be used to admit or extract substances to or from the tank 1101. Each aperture or port 1131, 1132 preferably has an associated supply line 1133, 1134, sealing element 1135, 1136, and coupling element 1137, 1138. The lower wall 1103 of the tank 1101 defines an outlet aperture or port 1172 preferably having an associated drain or outlet line 1174, sealing element 1176, and coupling element 1178.

In a variation of the foregoing sleeveless mixing assemblies 1000, 1100, a shaft may be interfaced to a tank via a rotatable sealing bearing (not shown) such as comprising a ball and socket joint. If provided, such a sealing bearing may comprise low friction polymeric materials (e.g., polytetrafluoroethylene) along mating surfaces. Multiple seals may be provided to prevent tank leakage.

While cylindrical mixing tanks 1001 and 1101 were illustrated and described in the preceding embodiments, it is to be appreciated that tanks of any suitable shape may be employed and include mixing components according to the present invention.

FIG. 15 illustrates a mixing assembly 1300 including a cylindrical mixing tank 1301 substantially similar to the tank 901 illustrated and described in connection with FIG. 11A. The tank 1301 preferably comprises a flexible polymeric film, and is preferably externally supported by a structure such as a rigid open cylindrical tank (not shown). The tank 1301 includes a cavity-defining sealed sleeve 1320 joined thereto (e.g., along the inner surface 1302 adjacent to the top wall 1304) and protruding into the tank 1301. The sleeve cavity 1323 contains a mixing paddle 1325 and support rod 1324. The function of the sleeve 1320 is to serve as an isolation barrier between the mixing elements 1324, 1325 and the interior 1302 of the tank. If desired, the sleeve 1320 may be fabricated from a polymer film with a lower seam 1321 provided after the mixing elements 1324, 1325 are inserted into the sleeve 1320, such that any of the mixing elements 1324, 1325 may be permanently retained by the sleeve 1320. The sleeve 1320 may include a reinforced aperture-defining coupling guide 1328 to permit the support rod 1325 to be inserted into the sleeve 1320 and/or permit an external mixing mechanism (not shown) to be coupled to the support rod 1325 while resisting puncture or damage of the sleeve 1320. In operation, the paddle 1325 and rod 1324 contained within the sleeve 1325 are preferably directed in a substantially circular path at a nonzero angle relative to a substantially central vertical of the tank 1301 to stir or admix substances contained therein.

An upper seam 1322 preferably joins the sleeve 1320 to the tank 1301, with the sleeve 1320 preferably permanently joined to the tank 1301 such as by welding. Both the tank 1301 and sleeve 1320 preferably comprise polymeric materials suitable for economical single use (i.e., disposable) operation. In one embodiment, each of the tank 1301 and sleeve 1320 comprises a polymeric film; in a particularly preferred embodiment, each of the tank 1301 and sleeve 1320 comprises a substantially optically transmissive or transparent film. If desired, a substantially open external frame (not shown) may be provided to support the tank 1301 with associated hooks or connectors (not shown). The upper wall 1304 of the tank 1301 further defines apertures 1331, 1332 serving as access ports, such as may be used to admit or extract substances to or from the tank 1301. Each aperture or port 1331, 1332 preferably has an associated supply line 1333, 1334, sealing element 1335, 1336, and coupling element 1337, 1338. The lower wall 1310 of the tank 1301 defines an outlet aperture or port 1372 preferably having an associated drain or outlet line 1374, sealing element 1376, and coupling element 1378. In this manner, the tank 1301 may be joined to other elements of a processing system (not shown), and substances exchanged therebetween may be processed.

Another embodiment is directed to a method for fabricating a mixing apparatus. Referring to FIGS. 16A-16D, a mixing apparatus such as provided hereinabove may be fabricated in multiple steps. FIG. 16A illustrates an assembly view of an upper wall 1404 of a mixing tank and a sleeve 1413. The upper wall includes an aperture-defining coupling guide 1428, a substance access port 1460, and a second port 1431. The sleeve 1413, which may be fabricated of two sheets 1420A, 1420B of polymeric film materials, is sealed along the sides thereof (e.g., by welding) with each end being open. Thereafter, the free ends of the sheets 1420A, 1420B defining one open end of the sleeve 1413 are registered to the aperture defined in the coupling guide 1428, and are may be welded or otherwise joined to the underside of the top wall 1404 to form a joint 1415, such as shown in FIG. 16B, with the lower end 1421 of the sleeve 1413 remaining open. FIG. 16C illustrates an assembly view of the joined sleeve/mixing tank top wall of FIG. 16B, with a shaft 1424 and mixing paddle 1425 being inserted into the open end 1421 of the sleeve 1420. FIG. 16D shows the resulting assembly following sealing of the lower end 1421 of the sleeve 1413 with a joint 1417 such as a weld line.

Another embodiment is directed to a mixing apparatus including a volumetric compensation system adapted to maintain the internal volume of a flexible mixing tank within predetermined limits. Such a flexible mixing tank is preferably supported by an external container. Referring to FIGS. 17A-17D, an apparatus 1500 including volumetric compensation utility is illustrated in four states of operation. As described hereinabove, a mixing tank 1501 may comprise a flexible tank wall material. In response to differential pressure, the volume of such a tank 1501 when sealed is subject to change—causing it to expand or contract. A common cause of low pressure leading to tank volume contraction is the draining of liquid from a closed tank. Certain applications require substantially constant mixing while components are drained from the tank 1501. Taken to an extreme, volumetric contraction of the tank will 1501 will cause the tank walls to contact the paddle 1525 or shaft 1524, thus preventing further mixing.

To avoid tank collapse problems, fluid (e.g., gas) may be added to the tank 1501 while mixed contents are drained. To maintain sterile conditions within the tank 1501, all gas that is added to the tank 1501 is supplied through a sterile filter 1551. Such filters 1551, however typically have a substantial pressure drop that far exceeds the maximum pressure condition of a film-based flexible mixing tank 1501; thus the risk of performing uncontrolled gas addition is unacceptable, since dangerous overpressure conditions could result in tank rupture or explosion. The use of simple pressure regulation may be impracticable, however, due to difficulties in reliably and economically interfacing a pressure sensor with a disposable film-based tank wall material. To promote safe operation while avoiding the use of pressure sensing elements, a volumetric compensation system is provided in FIGS. 17A-17D.

Referring to FIG. 17A, a tank 1501 contains a liquid 1498 and a gas or vapor 1497. The tank includes a mixing paddle 1525 and associated shaft 1524 for mixing the contents of the tank 1501. The bottom wall of the tank 1501 includes a selectively operable drain 1572. The top wall 1504 of the tank 1501 includes a gas inlet 1531, a sterile filter 1551, a control valve 1550, and a pressurized gas supply 1555. The top wall 1504 further includes a plunger 1561 in at least intermittent contact with the top wall 1504, such that the plunger is adapted to move responsive to said tank wall deflection, with a contactor 1562 being in at least intermittent contact with the plunger 1561 to provide (when appropriate) a signal via control line 1552 to the control valve 1550.

In FIG. 17A, the tank 1501 is in a steady-state condition with no volumetric change from normal. This condition changes in FIG. 17B. As liquid 1498 is drained from the tank 1501, the volume of the tank 1501 contracts and the upper surface 1504 of the tank deflects or sags downward. Such downward deflection causes the plunger 1561 to drop relative to the contactor 1562. At a desired point, the plunger 1561 will activate the contactor 1562, initiating a first control signal via control line 1552 to open the control valve 1550 and/or activate the pressurized gas source 1555 to admit gas from the pressurized gas source 1555 through the valve 1550 and filter 1551 into the tank 1501. The source of pressurized gas may include any of a pressurized gas reservoir and a gas compressor, with particularly desirable gases including those being inert and relatively inexpensive, such as nitrogen or argon. In certain applications, air may be used.

Referring to FIG. 17C, as pressurized gas is added to the tank 1501, the downward deflection of the top wall 1504 is reversed—to the point that the top wall 1504 is deflected upward and the plunger 1561 is moved into a second sensory position relative to the contactor, which either severs the first control signal or initiates a second control signal via control link 1552 to close the control valve 1550 and/or deactivate the compressed gas source 1555 to stop the flow of gas into the tank 1501. As more liquid is drained from the tank, such as shown schematically by the downward arrow in FIGS. 17C-17D, the top wall 1504 of the tank 1501 returns to a neutral position such as shown in FIG. 17D.

In this manner, volumetric compensation system responsive to tank wall deflection is used to maintain the internal volume of the mixing tank within predetermined limits preferably while maintaining sterile conditions and avoiding the use of pressure-sensing elements.

Another embodiment is directed to a mixing paddle permanently joined to a shaft for use with a mixing apparatus. Referring to FIG. 18, a mixing element 1526 includes a paddle 1525 and a shaft 1524 joined with a welded seam 1529. A first end 1527A of the mixing element 1526 includes the paddle 1525, and a second end 1527 includes a radially protruding torque transfer pin 1528. Preferred materials of construction include metals, preferably stainless steel. Advantages of this mixing element 1526 relative to separable two-part elements include high strength, reusability, and elimination of paddle-shaft coupling difficulties within a mixing sleeve. The dimensions of the paddle are chosen to maintain good mixing functionality (i.e. with adequate paddle width) but permit the paddle to be inserted through the open (upper) registered apertures of a mixing sleeve and mixing tank. Preferably, the attached paddle width (i.e., including the shaft) is less than eight times the shaft diameter; more preferably, the attached paddle width is less than four times the shaft diameter.

Referring to FIGS. 19A-19C, a tank 1601 and mixing element 1526 are shown. The tank 1601 includes a bottom wall 1610 and a top wall 1604 to which a sealed sleeve 1640 having an aperture-defining upper end is attached. The paddle-containing first end 1527A (see FIG. 18) of the mixing element 1526 may be inserted into the sleeve 1640 to yield the mixing assembly 1600 of FIG. 19C. Such an assembly permits the mixing element 1526 to be re-used, and due to the presence of the sealed sleeve 1640, the mixing element 1526 need not be cleaned between uses.

A mixing tank 1700 according to another embodiment is illustrated in FIG. 20. The substantially parallelepiped-shaped tank 1700 includes an upper wall 1704 defining an aperture-containing coupling guide 1728 leading to a sealed sleeve 1740, and defining a substance port 1760 and secondary port 1731. Side walls 1730 in conjunction with the upper and lower walls 1704, 1710 define the interior volume 1780 that is further bounded by the exterior surface of the sleeve 1740. The sleeve 1740 is substantially cylindrical in shape and adapted to receive the mixing element 1526 described previously. The lower wall 1710 includes a drain flange 1771 and plunger 1770 leading to a drain line 1774. Further details regarding the drain connector inclusive of the flange 1771, plunger 1770 and drain line 1774 may be found in commonly assigned U.S. Patent Application No. 60/718,466 filed Sep. 19, 2005 and entitled "Drain Connector for Substance Processing Receptacle," which application is hereby incorporated by reference herein.

While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A mixing apparatus comprising:
   a hollow mixing tank having at least one interior wall bounding an internal volume;
   a first rod insertion element disposed along a surface of the mixing tank; and
   a first sleeveless mixing paddle adapted to engage a first support rod extending through the first rod insertion element and mechanically coupleable to receive kinetic energy from at least one kinetic energy source, the first mixing paddle having at least one widened paddle portion that is wider than a nominal diameter or cross-sectional width of the first support rod;
   wherein the first rod insertion element inhibits continuous rotation of the first support rod about a longitudinal axis thereof and serves to isolate the internal volume from a surrounding environment;
   wherein the first rod insertion element comprises a first reinforcing flange affixed to the first support rod, and comprises a first non-rotating sealed joint between the first reinforcing flange and the at least one interior wall; and
   wherein the mixing apparatus is adapted for coupling with a gas source, and the mixing apparatus further comprises a filter medium arranged to eliminate biological contaminants from gas supplied to the internal volume from the gas source.

2. The mixing apparatus of claim 1, wherein the first mixing paddle includes a first narrow paddle portion that is narrower than the at least one widened paddle portion of the first mixing paddle, and that extends from the at least one widened paddle portion of the first mixing paddle toward the first rod insertion element.

3. The mixing apparatus of claim 1, wherein the mixing tank comprises a polymeric film.

4. The mixing apparatus of claim 1, wherein the mixing tank defines at least one resealable access port.

5. The mixing apparatus of claim 1, wherein the first reinforcing flange comprises a polymeric sheet.

6. The mixing apparatus of claim 1, wherein the first non-rotating sealed joint comprises a welded joint.

7. The mixing apparatus of claim 1, adapted for movement of the first paddle within the internal volume through a defined path at a nonzero angle relative to an axis perpendicular to the first rod insertion element without continuous rotation of the first support rod.

8. The mixing apparatus of claim 7, wherein the defined path comprises a substantially circular path.

9. The mixing apparatus of claim 1, further comprising a volumetric compensation system adapted to maintain the internal volume of the mixing tank within predetermined limits.

10. The mixing apparatus of claim 1, wherein the first support rod is hollow.

11. A method utilizing a mixing apparatus according to claim 1, the method comprising supplying at least two materials to the internal volume, and operating the kinetic energy source to move the mixing paddle within the internal volume to combine at least two materials to form a mixture.

12. A mixing apparatus comprising:
    a mixing tank including at least one wall comprising a polymeric film and bounding an internal volume;
    a mixing paddle within the internal volume and engaged to a support rod or shaft extending through the at least one wall; and
    a mixing mechanism comprising a motor arranged to rotate an offset coupling, wherein the offset coupling is coupled to the support rod or shaft, and
    wherein the motor and offset coupling are arranged to move the support rod or shaft with a pivotal motion to cause the mixing paddle to move within the internal volume.

13. A mixing apparatus according to claim 12, wherein the polymeric film is substantially transparent.

14. A mixing apparatus according to claim 12, wherein the mixing paddle is sleeveless and is arranged to directly contact any contents contained in the internal volume.

15. A mixing apparatus according to claim 12, wherein the mixing tank defines at least one of a resealable access port and a drain port.

16. A mixing apparatus according to claim 12, further comprising a reinforcing flange affixed to the support rod or shaft and affixed to a wall of the mixing tank, and a non-rotating sealed joint between the reinforcing flange and the wall.

17. A mixing apparatus according to claim 12, wherein the mixing tank comprises a mixing bag.

18. A mixing apparatus according to claim 12, wherein the mechanism is arranged to cause the mixing paddle to move in an arcuate path within the internal volume without continuous rotation of the support rod or shaft about a longitudinal axis of the support rod or shaft.

19. A mixing apparatus according to claim 18, wherein the arcuate path is substantially circular.

20. A mixing apparatus according to claim 12, further comprising a support frame arranged to support the mixing tank and the mixing mechanism.

21. A mixing apparatus according to claim 12, wherein the mixing paddle comprises at least one widened portion that is wider than a nominal diameter or width of the support rod or shaft.

22. A mixing apparatus according to claim 12, wherein the support rod or shaft is hollow.

23. A mixing apparatus according to claim 12, further comprising a pivot guide arranged below the offset coupling, wherein the pivot guide is arranged to engage the support rod or shaft.

24. A mixing apparatus according to claim 12, adapted for coupling with a gas source, the apparatus further comprising a filter medium arranged to eliminate biological contaminants from gas supplied to the internal volume from the gas source.

25. A mixing apparatus according to claim 12, further comprising a computer processor arranged to control operation of the mixing mechanism.

26. A method utilizing a mixing apparatus according to claim 12, the method comprising supplying at least two materials to the internal volume, and operating the mixing mechanism to combine at least two materials to form a mixture.

27. A mixing apparatus according to claim 12, further comprising a volumetric compensation system adapted to maintain the internal volume of the mixing tank within predetermined limits.

28. The mixing apparatus of claim 27, wherein the volumetric compensation system is responsive to tank wall deflection.

* * * * *